(12) United States Patent
Hilpert et al.

(10) Patent No.: US 6,403,346 B1
(45) Date of Patent: Jun. 11, 2002

(54) ENZYMATIC PROCESSES FOR PRODUCING INTERMEDIATES USEFUL IN THE MANUFACTURE OF RETIFEROL DERIVATIVES

(75) Inventors: Hans Hilpert; Beat Wirz, both of Reinach (CH)

(73) Assignee: Basilea Pharmaceutica AG, Binningen (CH)

( * ) Notice: Subject to any disclaimer, the term of this patent is extended or adjusted under 35 U.S.C. 154(b) by 0 days.

(21) Appl. No.: 09/947,891

(22) Filed: Sep. 6, 2001

Related U.S. Application Data

(62) Division of application No. 09/817,465, filed on Mar. 26, 2001, which is a division of application No. 09/678,866, filed on Oct. 3, 2000, now Pat. No. 6,310,262.

(30) Foreign Application Priority Data

Oct. 18, 1999 (EP) .............................. 99120603

(51) Int. Cl.[7] .............................. C12P 7/62; C12P 7/40; C12P 9/00; C12P 7/24; C12P 7/26; C07C 49/105; C07C 45/00; C07C 69/63; C07C 69/02

(52) U.S. Cl. ........................ 435/135; 560/129; 560/226; 560/227; 560/231; 560/228; 568/376; 568/388; 568/389; 435/135; 435/131; 435/136; 435/147; 435/148

(58) Field of Search ................................ 560/228, 129, 560/226, 227, 231; 568/376, 388, 389; 435/135, 131, 136, 147, 148

(56) References Cited

U.S. PATENT DOCUMENTS 5,886,233 A * 3/1999 Steinmeyer et al. ........ 568/376

FOREIGN PATENT DOCUMENTS

| EP | 0 516 410 | 12/1992 |
| WO | 99 43646 | 9/1999 |

OTHER PUBLICATIONS

Negishi E., King A.O., Tour J.M., *Org. Synth.*, 64, pp. 44–49 (1986).

Alexakis A., Gardette M., Colin S., *Tetrahedron Letters*, 29, pp. 2951–2954 (1988).

Perlman, K.L., et al., *Tetrahedron Letters*, 32, pp. 7663–7666 (1991).

* cited by examiner

*Primary Examiner*—Samuel Barts
*Assistant Examiner*—Elvis O. Price
(74) *Attorney, Agent, or Firm*—George W. Johnston; John P. Parise

(57) ABSTRACT

Enzymatic processes can produce intermediates for manufacturing retiferol derivatives that are useful for treating or preventing hyperproliferative skin diseases and for reversing conditions associated with photodamage. These processes can use as a starting material trihydroxycyclohexane, which can be chemically modified by a process that includes an enzymatic step, typically involving lipases of EC-class 3.1.1.3 or 3.1.1.34.

4 Claims, No Drawings

ENZYMATIC PROCESSES FOR PRODUCING INTERMEDIATES USEFUL IN THE MANUFACTURE OF RETIFEROL DERIVATIVES

CROSS REFERENCE TO RELATED APPLICATION

This is a divisional of patent applications Ser. No. 09/817,465, filed Mar. 26, 2001, which is a divisional of Ser. No. 09/678,866, filed Oct. 3, 2000 now U.S. Pat. No. 6,310,262.

BACKGROUND OF THE INVENTION

1. Field

The invention relates to a new process for the preparation of retiferol derivatives of the formula:

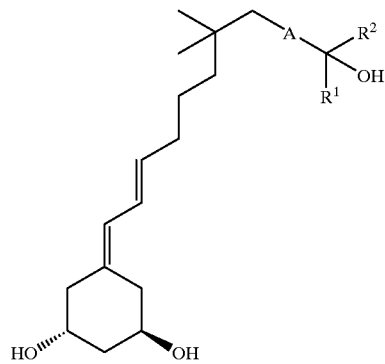

wherein

A is —C≡C— or —CH=CH—, and $R^1$ and $R^2$ are independently of each other lower alkyl or lower perfluoroalkyl.

2. Description

Compounds of formula I can be utilized to treat or prevent hyperproliferative skin diseases such as psoriasis, basal cell carcinomas, disorders of keratinization and keratosis neoplastic diseases and disorders of the sebaceous glands such as acne and seborrhoic dermatitis. The compounds of formula I can also be utilized in reversing the conditions associated with photodamage, particularly for the oral or topical treatment of the skin damaged through sun exposure, the effects of wrinkling, elastosis and premature aging, especially for the treatment of psoriasis. Such compounds are known and disclosed in WO 99/43646.

SUMMARY OF THE INVENTION

The subject invention provides a process for preparing a compound of the formula:

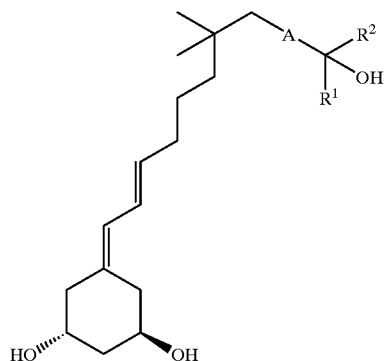

wherein A is —C≡C— or —CH=CH— and $R^1$ and $R^2$ each independently are lower alkyl or lower perfluoroalkyl. This process comprises coupling a compound of the formula:

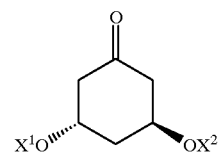

wherein $X^1$ and $X^2$ are hydroxy protecting groups, with a compound of the formula:

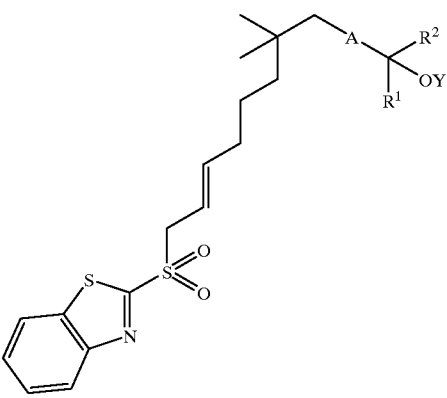

wherein A, $R^1$, $R^2$ are as above and Y is a hydroxy protecting group, to produce the compound of formula I. Preferred hydroxy protecting groups, $X^1$ and $X^2$, are $Si(C_1-C_4\text{-alkyl})Me_2$ or a group $R^3CO$— where $R^3$ is lower alkyl or mono-chlorinated lower alkyl and Y is $Si(C_1-C_4\text{-alkyl})_3$. It is also preferred where A is —CH=CH—.

The subject invention also provides a process for preparing a compound of the formula:

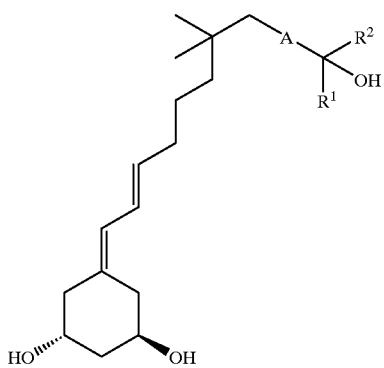

I wherein A is —C≡C— or —CH=CH— and $R^1$ and $R^2$ each independently are lower alkyl or lower perfluoroalkyl. The process comprises coupling a compound of formula:

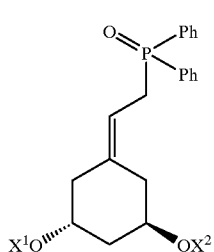

IV wherein $X^1$ and $X^2$ are hydroxy protecting groups, with a compound of formula:

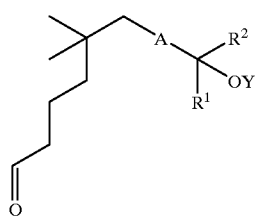

V wherein A, $R^1$, $R^2$ are as above and Y is a hydroxy protecting group to produce the compound of formula I. Favorably, $X^1$ and $X^2$ are each independently Si($C_1$–$C_4$-alkyl)Me$_2$ or a group $R^3$CO— where $R^3$ is lower alkyl or mono-chlorinated lower alkyl and Y is Si($C_1$–$C_4$-alkyl)$_3$. It is also preferred that A is —CH=CH—.

Another process provided by the subject invention is for preparing a compound of the formula:

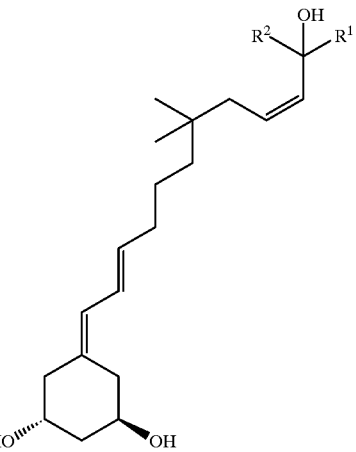

Ia wherein $R^1$ and $R^2$ are each independently lower alkyl or lower perfluoroalkyl. This process comprises coupling a compound of formula:

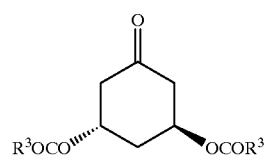

IIa wherein $R^3$ is lower alkyl or mono-chlorinated lower alkyl, with a compound of formula:

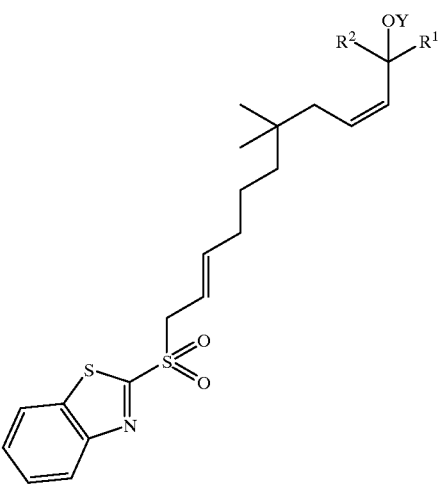

IIIa wherein $R^1$, $R^2$ are as above and Y is a Si($C_{1-4}$-alkyl)$_3$. The protected hydroxy groups are then deprotected to obtain a compound of formula Ia.

Yet another inventive process is for preparing a compound of the formula:

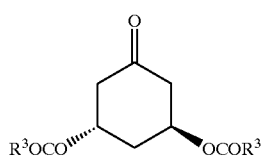

wherein R³ is lower alkyl or mono-chlorinated lower alkyl. This process involves protecting the hydroxy groups of the trans/cis/trans compound of the formula:

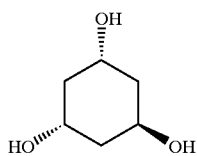

or protecting the hydroxy groups of the all cis 1,3,5-trihydroxycyclohexane, to obtain the compound of the formula:

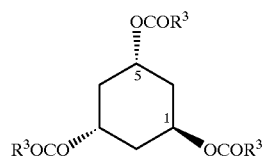

wherein R³ is lower alkyl or mono-chlorinated lower alkyl). In the case of the all cis 1,3,5-trihydroxycyclohexane, this involves obtaining the protected all cis 1,3,5-trihydroxycyclohexane wherein the hydrogen atoms of the hydroxy groups have been replaced by R³ as above. The R³CO-group is then hydrolyzed in the 5-position in a biphasic water/organic solvent system in an enzymatic reaction to obtain a product of the formula:

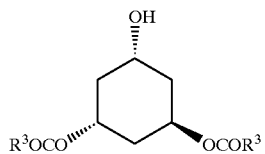

wherein R³ is as above. The hydroxy group o this compound is then oxidized to obtain a compound of formula IIa. The process beneficially uses enzymatic reaction lipases of the EC-class 3.1.1.3 or 3.1.1.34.

A further inventive process prepares a compound of the formula:

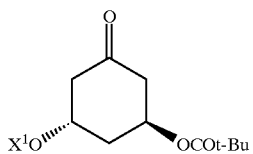

wherein X¹ is Si(C₁₋₄-alkyl)Me₂ or R³CO— where R³ is lower alkyl or mono-chlorinated lower alkyl. This process comprises protecting one hydroxy group of a compound of the formula:

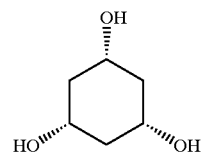

to obtain a compound of the formula:

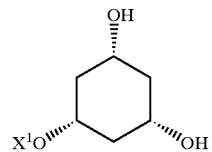

wherein X¹ is as above. This compound is then acylated via an enzyme at a further hydroxy group of a compound of the formula (3) in a non-aqueous acylation solvent to obtain a compound of the formula:

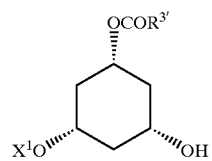

wherein X¹ is as above and R³' is methyl. The configuration of the carbon atom which carries the remaining unprotected hydroxy group in compound of formula (4) is then inverted and the R³'OC— group is cleaved to form a hydroxy derivative. The hydroxy group is then oxidized to obtain a compound of formula IIb. A preferred enzyme is a lipase of the EC-class 3.1.1.3 or lipoprotein lipases of the EC-class 3.1.1.34.

Another inventive process is for preparing a compound of the formula:

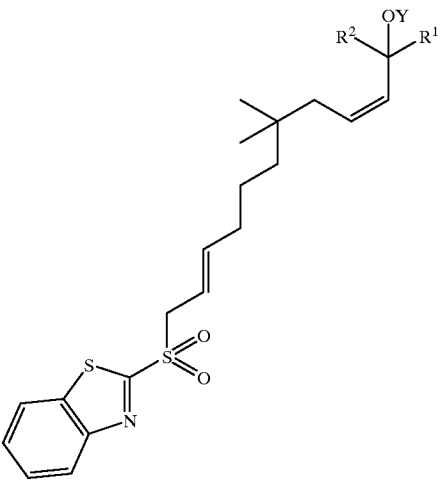

wherein $R^1$, $R^2$ are each independently lower alkyl or lower perfluoroalkyl and Y is $Si(C_{1-4}\text{-alkyl})_3$. This process comprises reacting a compound of the formula:

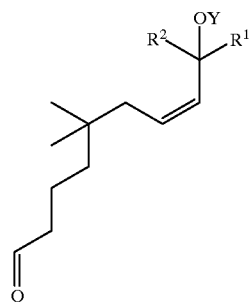

Va wherein $R^1$, $R^2$ and Y are as above, with $Me_3SiCH_2CO_2R^5$, $Ph_3P=CH—CO_2R^5$ or $(EtO)_2P(O)CH_2CO_2R^5$, wherein $R^5$ is lower alkyl; to obtain the compound of the formula:

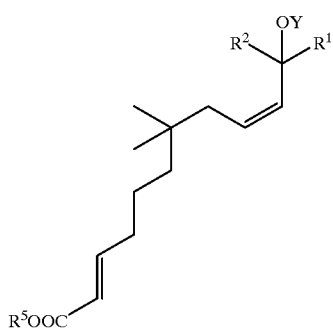

10 wherein $R^1$, $R^2$, $R^5$ and Y are as above. The ester group is then reduced to obtain the hydroxy derivative of the compound of formula (10). This is coupled with 5-mercapto-1-phenyltetrazole or 2-mercapto-benzothiazole to obtain the compound of the formula:

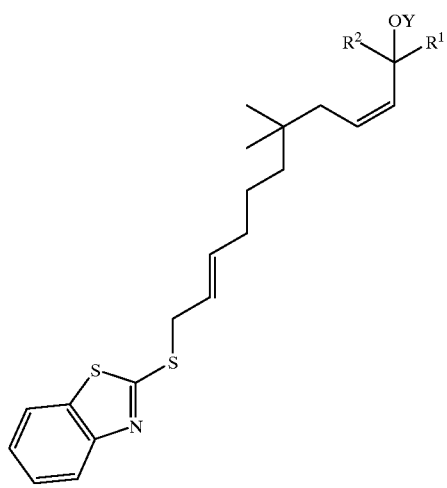

11 wherein $R^1$, $R^2$ and Y are as above, The sulfanyl group of the compound of the formula 11 to then oxidized to obtain the compound of formula IIIa.

The subject invention provides a compound of the formula:

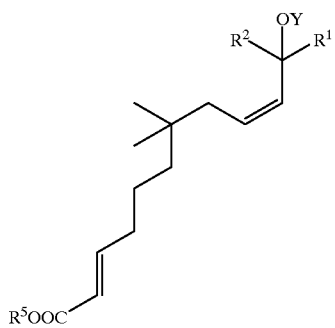

10 wherein $R^1$ and $R^2$ are each independently lower alkyl or lower perfluoroalkyl, Y is $Si(C_{1-4}\text{-alkyl})_3$ and $R^5$ is a lower alkyl.

In addition, the invention provides a compound of the formula:

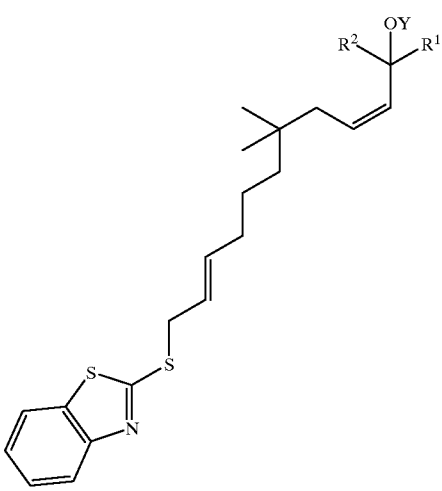

11 wherein $R^1$ and $R^2$ are each independently lower alkyl or lower perfluoroalkyl and Y is a $Si(C_{1-4}\text{-alkyl})_3$.

Also provided is a compound of the formula:

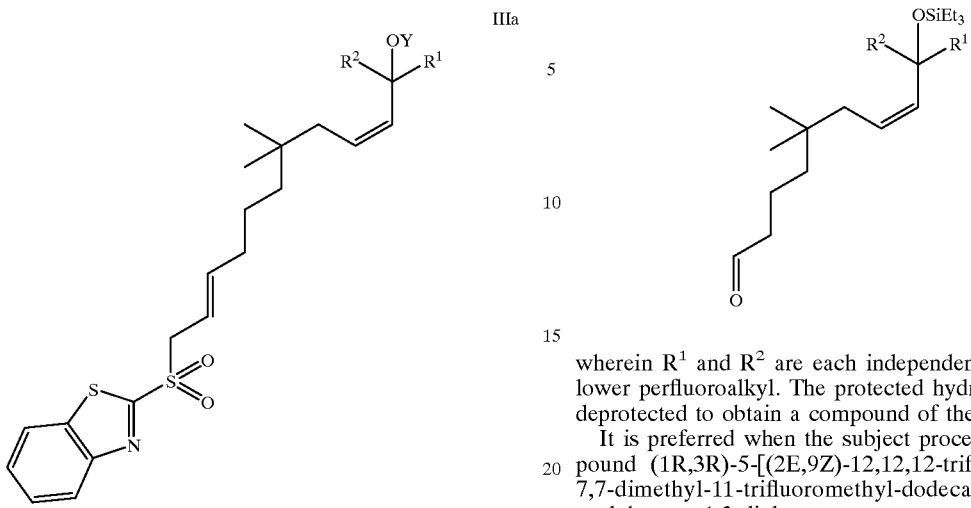

IIIa wherein $R^1$ and $R^2$ are each independently lower alkyl or lower perfluoroalkyl and Y is $Si(C_{1-4}\text{-alkyl})_3$.

Another inventive process is for preparing a compound of the formula:

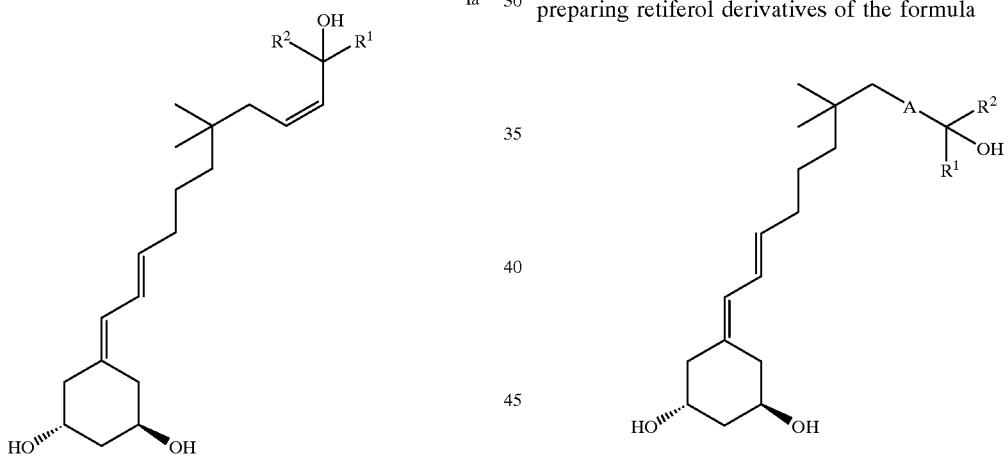

Ia wherein $R^1$ and $R^2$ are each independently lower alkyl or lower perfluoroalkyl. This process comprises coupling a compound of the formula:

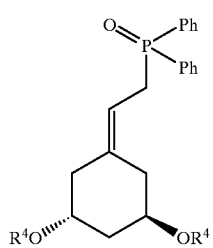

IVa wherein $R^4$ is a $Si(C_{1-4}\text{-alkyl})Me_2$ with compound of the formula:

Va wherein $R^1$ and $R^2$ are each independently lower alkyl or lower perfluoroalkyl. The protected hydroxy group is then deprotected to obtain a compound of the formula Ia.

It is preferred when the subject process forms the compound (1R,3R)-5-[(2E,9Z)-12,12,12-trifluoro-11-hydroxy-7,7-dimethyl-11-trifluoromethyl-dodeca-2,9-dienylidene)-cyclohexane-1,3-diol.

DETAILED DESCRIPTION OF THE PREFERRED EMBODIMENTS

The subject invention will now be described in terms of its preferred embodiments. These embodiments are set forth to aid and understand the invention but are not to be construed as limiting.

In general the invention relates to a new process for preparing retiferol derivatives of the formula

I wherein
A is —C≡C— or —CH=CH—, and
$R^1$ and $R^2$ are independently of each other lower alkyl or lower perfluoroalkyl.

The term "lower alkyl" as used herein denotes straight chain or branched alkyl residues containing 1 to 4 carbon atoms, such as methyl, ethyl, propyl, isopropyl, butyl, isobutyl or tert-butyl.

The term "lower perfluoroalkyl" denotes lower alkyl groups as defined above wherein the hydrogen atoms are substituted by fluorine, such as in trifluoromethyl, pentafluoroethyl, perfluoropropy, and the like.

In the structural formulas presented herein, a broken bond (·····) denotes that the substituent is below the plane of the paper and a wedged bond (◢) denotes that the substituent is above the plane of the paper.

Although compounds of formula I can be prepared as described in WO 99/43646, these compounds can be prepared more efficiently in a lower number of reaction steps and in a higher yield by the inventive processes depicted in scheme A, namely by method A which comprises the coupling of ketones of formula II with compounds of formula III or by method B which comprises the coupling of phosphinoxides of formula IV with aldehydes of formula V, method B, which comprises the coupling of phosphinoxides of formula IV with aldehydes of formula V.

The preferred method for the preparation of retiferol derivatives of formula I, wherein A is a double bond (compounds of formula Ia) according to scheme 1, is by coupling of the ketones of formula II, wherein $X^1$ and $X^2$ are $R^3CO$— groups (compounds of formula IIa), with com Scheme A:

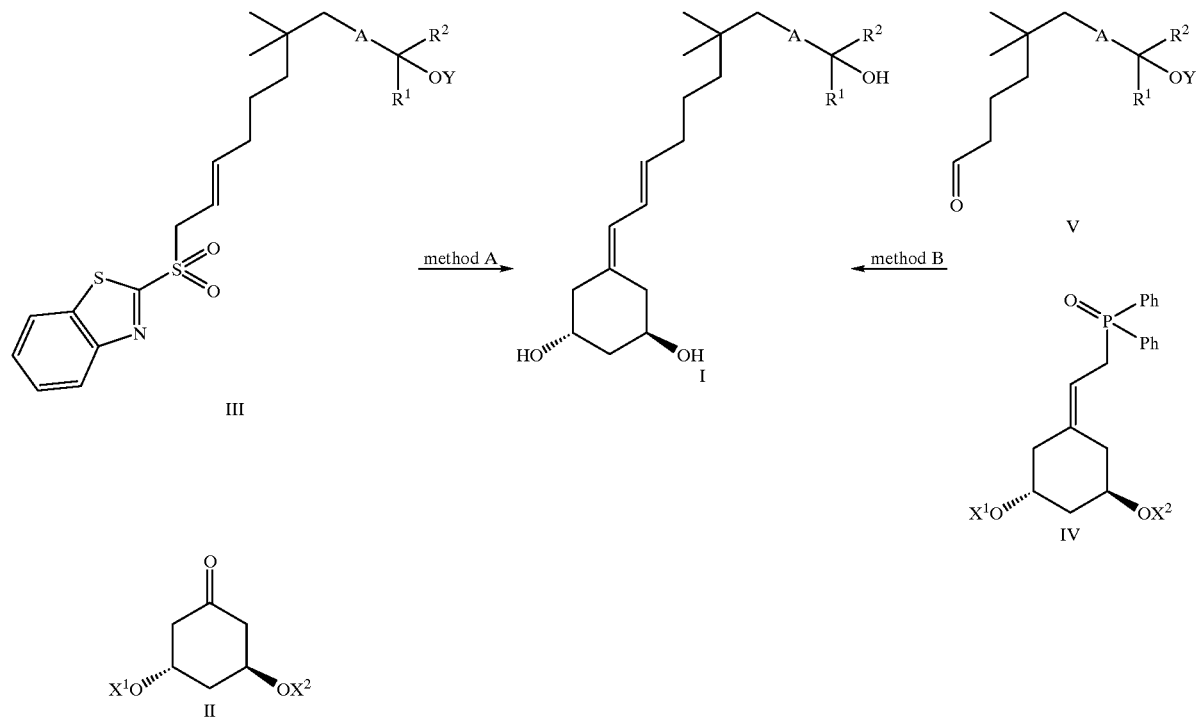

wherein A, $R^1$ and $R^2$ are as defined above and $X^1$, $X^2$ and Y are hydroxy protecting groups.

The "hydroxy protecting groups" as used herein are for $X^1$ and $X^2$ independently of each other a mono alkyl dimethyl-silyl group [Si($C_{1-4}$-alkyl)Me$_2$], preferably a tert-butyldimethyl-silyl group (TBS) or an acyl group ($R^3CO$—), wherein $R^3$ signifies lower alkyl or mono chlorinated lower alkyl; and for Y a trialkyl-silyl group [Si($C_{1-4}$-alkyl)$_3$], preferably a triethyl-silyl group (SiEt$_3$) or a trimethyl-silyl group (SiMe$_3$).

The term "mono chlorinated lower alkyl" as used herein denotes straight chain or branched alkyl residues containing 1 to 4 carbon atoms with one chloro atom, such as chloromethyl, chloroethyl, chloropropyl, chloroisopropyl, chlorobutyl, chloro isobutyl or chloro tert-butyl.

The invention is thus concerned with new processes for the preparation of compounds of formula I, according to scheme A, by method A, which comprises the coupling of ketones of formula II with compounds of formula III or by pounds of formula III, wherein A is a double bond (compounds of formula IIIa) according to method A in a two-step reaction, Scheme 1:

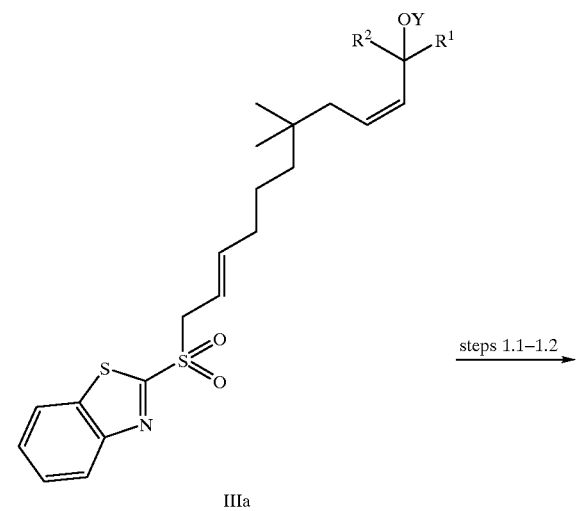

steps 1.1–1.2

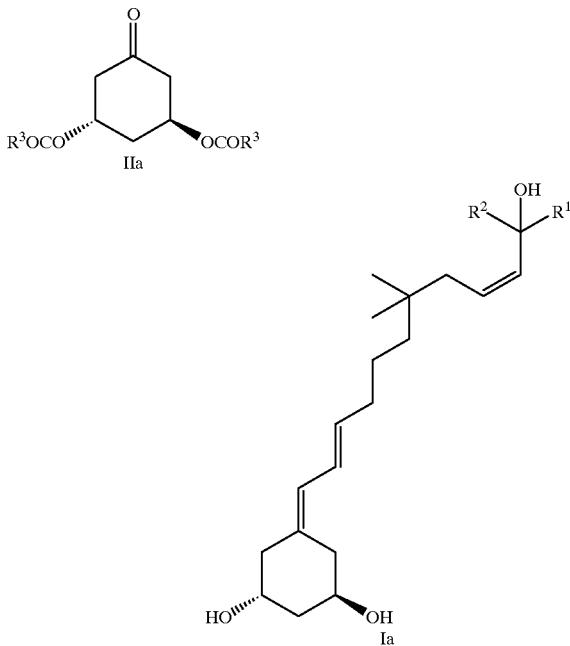

where the symbols are as defined above.

In step 1.1, the bis-acylated ketone of formula IIa is coupled with a compound of formula IIIa in the presence of a strong base, obtaining a fully hydroxy group protected derivative of the compound of formula Ia.

As a strong base n-butyl lithium (n-BuLi) or lithium diisopropylamide (LDA) can be used, a preferred strong base is $LiN(SiMe_3)_2$.

The reaction is carried out in solvents such as hydrocarbons preferably toluene, or ethers, an especially preferred solvent is tetrahydrofuran (THF); at a reaction temperature from −100° to +60°, an especially preferred temperature range is −80° to 20°.

In step 1.2, the fully hydroxy group protected derivative of the compound of formula Ia is reacted in the presence of a base to cleave the protecting groups to form the retiferol compound of formula Ia.

Bases for the deprotection reaction in step 1.2 are KOH, NaOH, $Na_2CO_3$ or $NH_4OH$, preferably $K_2CO_3$.

The reaction is carried out in solvents such as $C_1$–$C_6$ alcohols, or water, or mixtures of the mentioned $C_1$–$C_6$ alcohols with water, a preferred solvent is MeOH; at a reaction temperature from −10 to +50°, especially preferred at 20°.

The term "$C_1$–$C_6$ alcohols" as used herein denotes straight chain or branched alkyl residues containing 1 to 6 carbon atoms with one hydroxy group, such as methanol, ethanol, propanol, isopropanol, butanol, isobutanol, tert-butanol, pentanol or hexanol.

Preferred are processes for the preparation of compounds of formula I wherein A is a double bond —C═C—, more preferred of compounds of formula I wherein A represents a cis configurated double bond, for example (1R,3R)-5-[(2E, 9Z)-12,12,12-trifluoro-11-hydroxy-7,7-dimethyl-11-trifluoromethyl-dodeca-2,9-dienylidene)-cyclohexane-1,3-diol.

In the following, the inventive processes for the preparation of the intermediates of formula II and III for the preparation of retiferol derivatives of formula I are described. The compounds of formula II may be prepared according to EP 0 516 410. However, it has been found that these compounds are prepared more effectively in a lower number of reaction steps and in a higher yield by the processes depicted in schemes 2 and 3, namely by new processes for the stereospecific synthesis of compounds of formula IIa and IIb.

The reaction depicted in scheme 2 is starting with commercially available trans/cis/trans 1,3,5-trihydroxycyclohexane of formula (a) optionally containing all cis 1,3,5-trihydroxycyclohexane, Scheme 2:

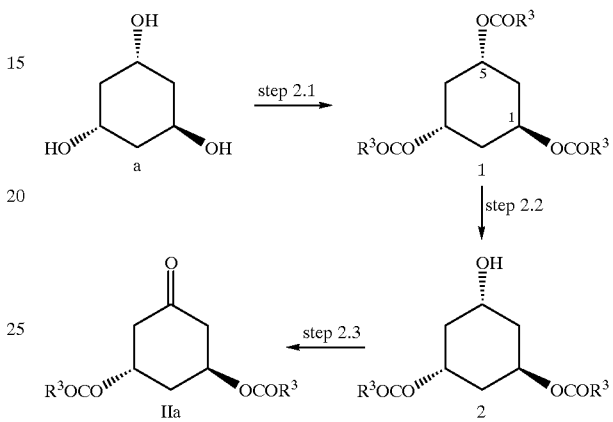

wherein $R^3$ is lower alkyl or mono chlorinated lower alkyl except the tert-butyl group.

In step 2.1, the hydroxy groups of trans/cis/trans 1,3,5-trihydroxycyclohexane of formula (a) and all cis 1,3,5-trihydroxycyclohexane are protected with $R^3CO$— groups, according to standard conditions, to obtain the acylated triol of formula (1) and acylated all cis 1,3,5-trihydroxycyclohexane.

In step 2.2, the protecting $R^3CO$— group in the 5-position of the trans isomer of the trans/cis/trans mixture of the acylated triol (1) is regio- and stereoselectively hydrolyzed by an enzymatic reaction to a mono hydroxy-bis acylated compound of formula (2), whereas the all cis isomer which may be present remains unreacted in the mixture and is removed. The reaction is carried out in water at a pH in the range of 6.5–8.0, preferably in the presence of an organic co-solvent.

The reaction is preferably carried out with a mixture of acylated trans/cis/trans 1,3,5-trihydroxycyclohexane of formula (1) and all cis 1,3,5-trihydroxycyclohexane.

For the above enzymatic reaction lipases of the EC-class 3.1.1.3 or 3.1.1.34 are used, preferably lipases from yeast of Genus Candida, especially preferred of *Candida rugosa* (former classification *C. cylindracea*).

Such lipases are commercially available as for example lipase MY and OF from Meito Sangyo, lipase AY from Amano, Chirazyme L-3 from Roche Diagnostics, Lipase F5 from Enzymatix (now: Chiroscience) or *C. rugosa*-lipases from Sigma or Fluka.

Preferred are the lipases MY, AY or Chirazyme L-3, especially preferred is the lipase OF.

The reaction is carried out in water, preferably in the presence of an organic co-solvent to obtain a biphasic water/organic solvent-system, which increases the selectivity and the activity of the lipases in the enzymatic reaction. Co-solvents for the reaction are non- or medium-polar solvents, such as alkanes or cycloalkanes, an especially preferred co-solvent is cyclohexane.

The reaction is further characterized in that the aqueous system contains the biochemically usual salts, such as NaCl or KCl in a concentration of 0.1–0.5 M, preferred 0.1 M, at a pH in the range of 6.5–8.0, buffered by 2–20 mM solutions of sodium or potassium phosphate.

Instead of the above salts, ingredients such as LiSCN, Na$_2$SO$_4$ or polyhydric alcohols or carbohydrates such as D-glucose can be used at the same concentration.

In a further aspect of step 2.2, the lipases can be used in an immobilized form.

The substrate concentration in this reaction is in the range of 1–20%, preferably in the range of 1–10%.

The reaction temperature for the above reaction is between the freezing point of the system and ambient temperature, preferably the temperature is close to the freezing point of the system.

In step 2.3, the unprotected hydroxy group of mono hydroxy-bis acylated compounds of formula (2) is oxidized in the presence of an oxidant to form bis acylated ketones of formula IIa.

The oxidation is carried out in the presence of oxalyl chloride and dimethyl sulfoxide (DMSO) (Swern method), 1,3-Dicyclohexylcarbodiimide (DCC) and DMSO (Pfitzner-Moffatt method), pyridine-SO$_3$-complex and DMSO or (CH$_3$)$_2$S with N-chlorosuccinimide (Corey-Kim method), a preferred oxidation method is the oxidation with NaOCl in the presence of 2,2,6,6-tetramethylpiperidin-1-oxyl radical (TEMPO) as a catalyst.

The reaction is carried out in solvents such as ethers e.g. tert-butyl methyl ether (TBME), esters e.g. ethyl acetate, hydrocarbons e.g. toluene, or halogenated hydrocarbons especially preferred dichloromethane, at a reaction temperature from −100° to +50°, an especially preferred temperature for the NaOCl/TEMPO oxidation is 0°.

A further embodiment of the invention is the process for the preparation of compounds of formula II, wherein X$^1$ is as defined above except the MeCO-group and X$^2$ is a tert-butyl-CO— group (compounds of formula IIb). The reaction is carried out according to scheme 3, starting with commercially available all-cis 1,3,5-trihydroxycyclohexane of formula (b), according to standard conditions, to obtain the corresponding mono protected triol of formula (3).

This reaction is preferably carried out with tert-butyldimethylsilyl triflate (TBSOTf) as protecting reagent, an especially preferred protecting reagent is tert-butyldimethylsilyl chloride (TBSCl). Both protecting reagents are yielding to mono protected compound of formula (3), wherein X$^1$ is a tert-butyldimethyl-silyl group (TBS).

In a preferred way, the above reaction is carried out with a mixture of bases such as NaH and NEt$_3$, in a molar ratio of 1.0:1.1, in solvents such as ethers, preferably THF and at a reaction temperature of −20° to +60°, especially preferred at a temperature of 20° to 50°.

In step 3.2, a further hydroxy group of compounds of formula (3) is protected by an enzymatic acylation reaction, in the presence of an enzyme, in a non-aqueous system using the acyl donor as a solvent and optionally with a co-solvent. The reaction leads regio- and stereoselectively to a mono bis protected compound of formula (4).

The reaction is further characterized in that the formation of a di-acylated derivative is suppressed, that compound of formula (4) is obtained in enantiomeric excess (ee) higher than 99% ee, that the enzyme can be recycled, and that the substrate concentration is in the range of 1–20%.

Preferred enzymes for the above enzymatic reaction are lipases of the EC-class 3.1.1.3 or lipoprotein lipases of the EC-class 3.1.1.34, preferred are microbial lipases from Geni such as Candida, Pseudomonas, Alcaligenes, Aspergillus, Rhizopus, Penicillium, Humicola (newly classified as Thermomyces), Chromobacterium, Burkholderia or Mucor. Lipase from pig pancreas is also suitable.

Commercial available examples for lipases, which can be used in this reaction are: *Candida rugosa* (former classified as *C. cylindracea*) from Meito Sangyo (lipase MY or OF), from Amano (lipase AY), from Roche Diagnostics (Chirazyme L-3), from Enzymatix (now: Chiroscience; lipase F5), from Sigma or Fluka, *Candida antarctica* from Novo (Lipase SP-525 and SP-526) or from Roche Diagnostics (Chirazyme L-2 and L-5), from *Candida utilis* (Fluka), Pseudomonas (for example *P. cepacia, P. fluoreszens* and Scheme 3:

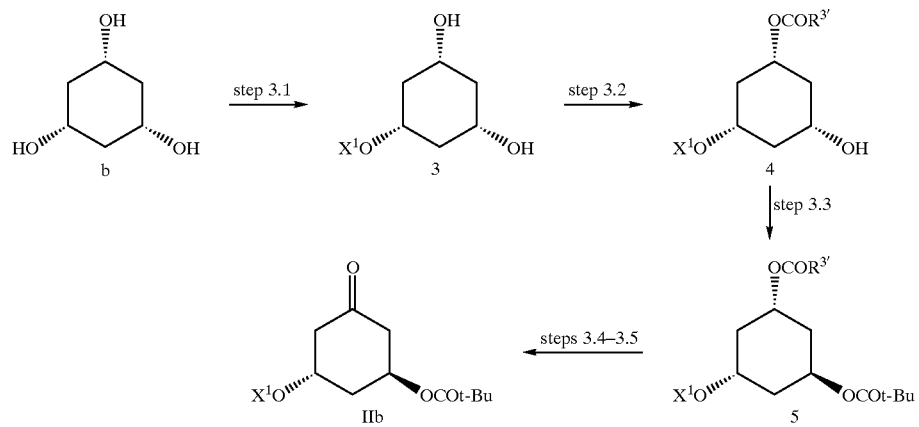

wherein the symbols are as defined above and R$^{3'}$ is a methyl group.

In step 3.1, one hydroxy group of cis-cyclohexane-1,3,5-triol of formula (b) is protected in the presence of a base, others) from Amano (lipase PS or AK), from Toyobo (lipase LPL-311), from Roche Diagnostics (Chirazyme L-6), from Fluka (lipase SAM) or from Enzymatix (lipase B1), Alcaligenes sp. from Meito Sangyo (lipase PL or QL), *Aspergillus* niger from Amano (lipase AP), *Rhizopus delemar* from Amano (lipase D), from *Penicillium camemberti* (former *P. cyclopium*) from Amano (lipase G), *Humicola lanuginosa* from Amano (lipase CE) or Enzymatix (now: Chiroscience; lipase F13), *Chromobacterium viscosum* from Sigma or Toyo Jozo, Burkholderia sp. from Roche Diagnostics (Chirazyme L-1), *Mucor javanicus* from Amano (lipase M-AP) or *Mucor mieheifrom* Novo (Lipozyme IM-20) or from Roche Diagnostics (Chirazyme L-9).

A preferred lipase is Chirazyme L-6, an especially preferred lipase is QL.

In a further aspect of step 3.2 the lipases can be optionally used in an immobilized form.

In the above enzymatic reaction, the usual acyl donors such as esters or anhydrides can be used. The preferred acyl donors are those to carry out the acylation step irreversibly such as enol esters, e.g. vinyl ester or isopropenyl esters. Preferred solvents for the reaction are vinyl esters or ethyl acetate, an especially preferred solvent is vinyl acetate, or anhydrides preferably acetic anhydride.

The reaction is optionally carried out with co-solvents which are non polar up to medium polar like alkanes or cycloalkanes. Preferred co-solvents are ketones such as methyl isobutyl ketone, or aromatic solvents, ethers, preferably TBME or diisopropyl ether.

Preferably, the reaction is carried out in vinyl acetate or in a mixture of vinyl acetate in ethyl acetate with a concentration of vinyl acetate higher than 1 eq relatively to the substrate and at a reaction temperature from 0° to +40°, especially preferred at ambient temperature.

The term "enantiomeric excess" (ee) as used herein signifies the purity of a mixture of enantiomers and it is calculated according to known methods.

In step 3.3, the configuration of the carbon atom which carries the remaining unprotected hydroxy group in compound of formula (4) is inverted by reaction with tert-butyl-COOH, according to the Mitsunobu method, to obtain the fully protected triol of formula (5).

The reaction is carried out in the presence of $C_{1-4}$-alkyl azodicarboxylates and P(aryl)$_3$, especially preferred is isopropyl azodicarboxylate (for safety reasons) in the presence of triphenyl phosphane (PPh$_3$).

The term "aryl" as used herein signifies in the scope of the present invention a phenyl group or phenyl groups which are monosubstituted in the ortho-, meta- or para-position. Suitable substituents for the phenyl group are $C_{1-4}$-alkyl groups, preferably a methyl group, for example tolyl or xylyl.

The above reaction can be carried out in solvents such as ethers, e.g. THF; esters e.g. ethyl acetate; hydrocarbons e.g. toluene or halogenated hydrocarbons preferably dichloromethane; and at a reaction temperature from −60° to +60°, especially preferred at a temperature of 0°.

In step 3.4, the R$^3$OC— group of the fully protected triol of formula (5) is cleaved off to form the hydroxy derivative of the compound of formula (5).

The above reaction is carried out in the presence of a base. The bases, solvents and reaction temperature suitable for this reaction are as described in step 1.2.

In step 3.5, the oxidation of the deprotected hydroxy group of the derivative of the compound of formula (5) is carried out as described in step 2.3, obtaining the bis hydroxy protected ketone of formula IIb.

Another preferred aspect of the invention is the synthesis of intermediates of formula III, wherein A is a double bond (compound of formula IIIa) starting with compounds of formula (9), which are synthesized according to scheme 4, Scheme 4:

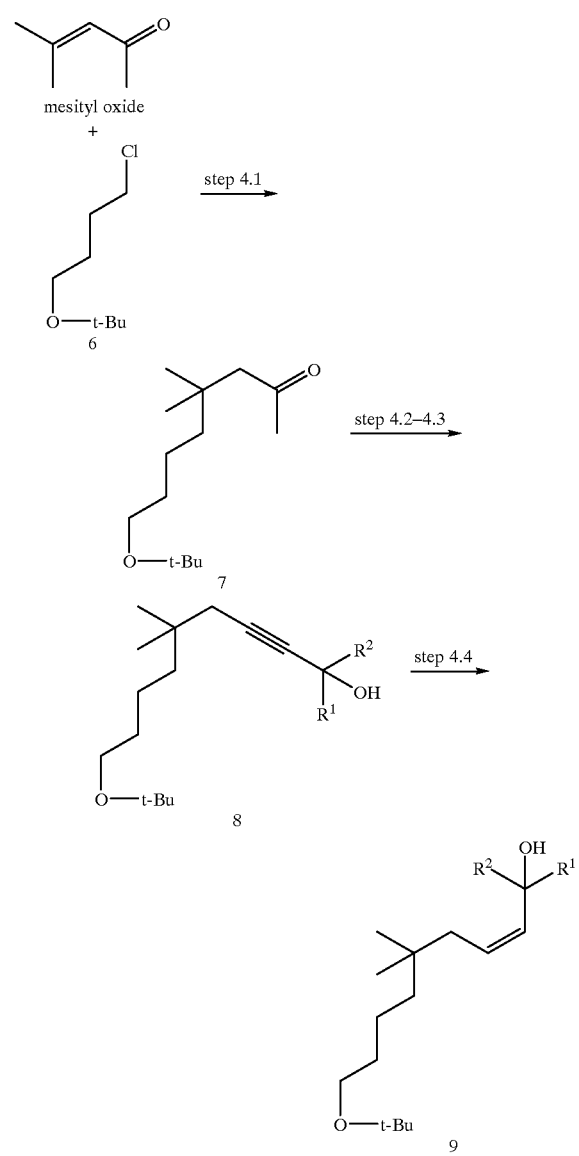

wherein the symbols are as defined above.

In step 4.1, 4-chlorobutyl-t.-butyl ether (6), which is prepared according to the method described in A. Alexakis, M. Gardette, S. Colin, Tetrahedron Letters, 29, 2951, 1988, is condensed with commercially available mesityl oxide in the presence of Mg and a catalyst, to obtain the compound of formula (7).

Catalysts in this reaction are CuCl or CuBr, a preferred catalyst is CuI in an amount of 1–100 mol %, preferably 10 mol %.

The reaction is carried out in solvents such as ethers, preferably in THF; at a reaction temperature from −80° to +80°, especially preferred at −20°.

In step 4.2, the compound of formula (7) is treated in a basic medium with HalP(O)(OR)$_2$, wherein Hal is a halogen such as Cl or Br and R is a lower-alkyl group or an aryl group, first to form an enolphosphate and subsequently to eliminate phosphate according to the method described in E. Negishi, A. O. King, J. M. Tour, *Org. Synth*. 64, 44,1986, to yield the anion of 8-tert-butoxy-4,4-dimethyl-oct-1-yne of formula:

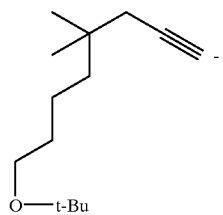

The reaction is carried out in the presence of a strong, non-nucleophilic base such as LiN(SiMe$_3$)$_2$, preferably lithium diisopropylamide (LDA).

The reaction is further carried out in solvents such as toluene or ethers, preferably THF and at a reaction temperature of –100° to –20° for the enolphosphate formation, preferably at –80°; and for the phosphate elimination at a reaction temperature of –20 to +60°, preferably at 20°.

In step 4.3, a ketone of formula O=CR$^1$R$^2$ is coupled with the anion of 8-tert-butoxy-4,4-dimethyl-oct-1-yne to obtain alkyne-ol derivatives of formula (8).

Preferred ketones of formula O=CR$^1$R$^2$ are those wherein R$^1$ and R$^2$ are independently of each other lower alkyl or lower perfluoroalkyl, especially preferred ketones are those wherein R$^1$ and R$^2$ are CF$_3$.

The reaction is carried out in the presence of a base and in a solvent as described in step 4.2, at a reaction temperature from –100° to –20°, preferably at a temperature of –80°.

In step 4.4, the alkyne-ol derivative of formula (8) is treated with hydrogen in the presence of a hydrogenation catalyst to obtain alkene compounds of formula (9), preferably a cis-configurated alkene compound of formula (9).

Such a hydrogenation catalyst is for example Palladium on carbon or a Lindlar catalyst, which is palladium on various supports, such as carbon, BaSO$_4$ or CaCO$_3$, poisoned with lead.

The hydrogenation is carried out in hydrocarbons such as toluene, or in esters such as ethyl acetate, or in ethers, preferably TBME, at a reaction temperature of –20° to +60°, a pressure of 10$^5$ to 10$^7$ Pa, preferably at a temperature of 22° and a pressure of 10$^5$ Pa.

Step 4.4 is omitted for the preparation of compounds of formula I wherein A is a triple bond.

Starting from compound of formula (9), the synthesis of compounds of formula IIIa is carried out according to the reaction depicted in scheme 5.

Scheme 5:

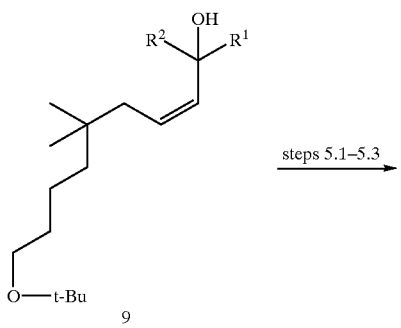

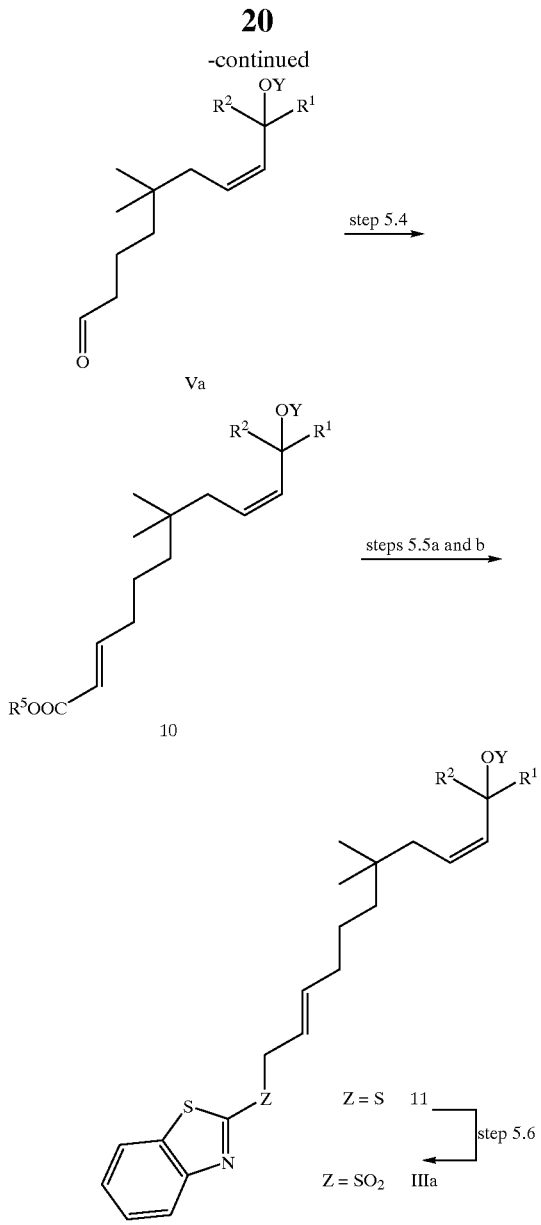

wherein the symbols are as defined above and R$^5$ is lower alkyl.

In step 5.1, alkene compounds of formula (9) are treated with an acid, to deprotect the protected hydroxy function and to form the hydroxy derivative of the compound of formula (9).

The acids used in this reaction are sulfonic acids such as toluene sulfonic acid, or strong mineral acids such as hydrochloric acid or phosphoric acid, an especially preferred acid is sulfuric acid. The solvents used in this reaction are as described for step 3.4.

In step 5.2, the deprotected hydroxy group of the derivative of formula (9) is then oxidized according to step 2.3, to obtain the corresponding aldehyde-derivative of compound of formula (9).

In step 5.3, the hydroxy group of the aldehyde is protected by reacting the compound with HalY, wherein Hal is a halogen such as Br or I, preferably Cl and Y is as defined above, preferably SiMe$_3$, especially preferred SiEt$_3$, to obtain the compound of formula Va.

The reaction in step 5.3 is carried out in the presence of a base and dimethylamino pyridine as an additive. Bases used in this reaction are amines such as NEt$_3$.

The reaction is carried out in solvents such as hydrocarbons, e.g. toluene; esters e.g. ethyl acetate, or ethers, preferably THF; at a reaction temperature from −20° to 60°, preferably at a temperature of 20°.

Compounds of formula Va are also used for the preparation of retiferol derivatives according to method B (see scheme 6 below).

In step 5.4, the compound of formula Va is reacted with commercial available $Me_3SiCH_2CO_2R^5$, $Ph_3P=CH—CO_2R^5$ or preferably $(EtO)_2P(O)CH_2CO_2R^5$ in the presence of a base to obtain the unsaturated ester derivative of formula (10), wherein $R^5$ is lower alkyl, preferably methyl or especially preferred ethyl.

Bases for the above reaction are strong, non-nucleophilic bases such as LDA or $LiN(SiMe_3)_2$, a preferred base is tert-butylOK.

The reaction is carried out in solvents such as ethers, preferably THF or hydrocarbons, an especially preferred solvent is toluene; at a reaction temperature from −100° to −20°, preferably at −80°.

Compounds of formula (10) are new and therefore form part of the invention. Preferred are compounds of formula (10) wherein Y is a $SiMe_3$ group, an especially preferred compound of formula (10) is wherein Y is a $SiEt_3$, $R^1$ and $R^2$ are $CF_3$ groups and $R^5$ is an ethyl group.

In step 5.5a, the ester group of the compound of formula (10) is reduced in the presence of a reducing reagent to form the hydroxy derivative of the compound of formula (10).

The reaction is carried out with commercially available reducing agents, such as Red-Al® or $LiAlH_4$, the preferred reducing agent is diisobutylaluminium hydride (DIBAH). In this reaction solvents are used, such as hydrocarbons, preferably toluene; ethers preferably, THF and the reaction temperature ranges from −100° to +60°, a preferred temperature is −80°.

In step 5.5b, the hydroxy derivative of the compound of formula (10), obtained through step 5.5a, is coupled with an activating agent in the presence of a base and a reagent according to the Mitsunobu method to obtain the sulfanyl-compound of formula (11).

The reaction is carried with commercially available activating reagents, such as 5-mercapto-1-phenyl-tetrazole, a preferred activating reagent is 2-mercapto-benzothiazole.

The reaction is carried out under the following conditions: in the presence of bases such as $PAr_3$, preferably $PPh_3$; with reagents such as $C_{1-4}$-alkyl azodicarboxylates, preferably isopropyl azodicarboxylates (for safety reasons); in solvents such as ethers, preferably THF; esters such as ethyl acetate; hydrocarbons such as toluene or halogenated hydrocarbons; at a reaction temperature from −60° to +60°, preferably at a temperature of 0°.

Compounds of formula (11) are new and therefore form part of the invention. Preferred are compounds of formula (11) wherein Y is a $SiMe_3$ group, especially preferred are compounds of formula (11) wherein Y is $SiEt_3$ and $R^1$ and $R^2$ are $CF_3$ groups.

In step 5.6, the sulfanyl-compounds of formula (11) are oxidized in the presence of an oxidant to obtain sulfonyl-compounds of formula IIIa.

Oxidation methods are oxidations in the presence of 3-chloroperbenzoic acid (MCPBA), Oxone® ($2KHSO_5.KHSO_4.K_2SO_4$) or $H_2O_2$ with ammonium heptamolybdate-tetrahydrate as a catalyst.

The reaction is carried out with solvents such as halogenated hydrocarbons, preferably $CH_2Cl_2$; or alcohols such as ethanol; at a reaction temperature from −20° to +70°, the preferred reaction temperature is in the range of 0° to 22°.

Compounds of formula IIIa are new and therefore form part of the invention. Preferred are compound of formula IIIa wherein Y is a $SiMe_3$ group, especially preferred are compounds of formula IIIa wherein Y is $SiEt_3$ and $R^1$ and $R^2$ are $CF_3$ groups.

Retiferol derivatives of formula I can also be prepared by the coupling of phosphinoxides of formula IV with aldehydes of formula V according to method B (scheme A). It has been found that with processes described below the yield for the preparation of retiferol derivatives of formula I is significantly increased.

A further aspect of the invention is thus the coupling of phophine oxides of formula IV, wherein $R^4$ is a mono alkyl dimethyl-silyl group $[Si(C_{1-4}\text{-alkyl})Me_2]$ (compounds of formula IVa) with aldehydes of formula V, wherein A is a double bond and Y a $SiEt_3$ group (compounds of formula Va) to obtain retiferol derivatives of formula Ia according to scheme 6, Scheme 6:

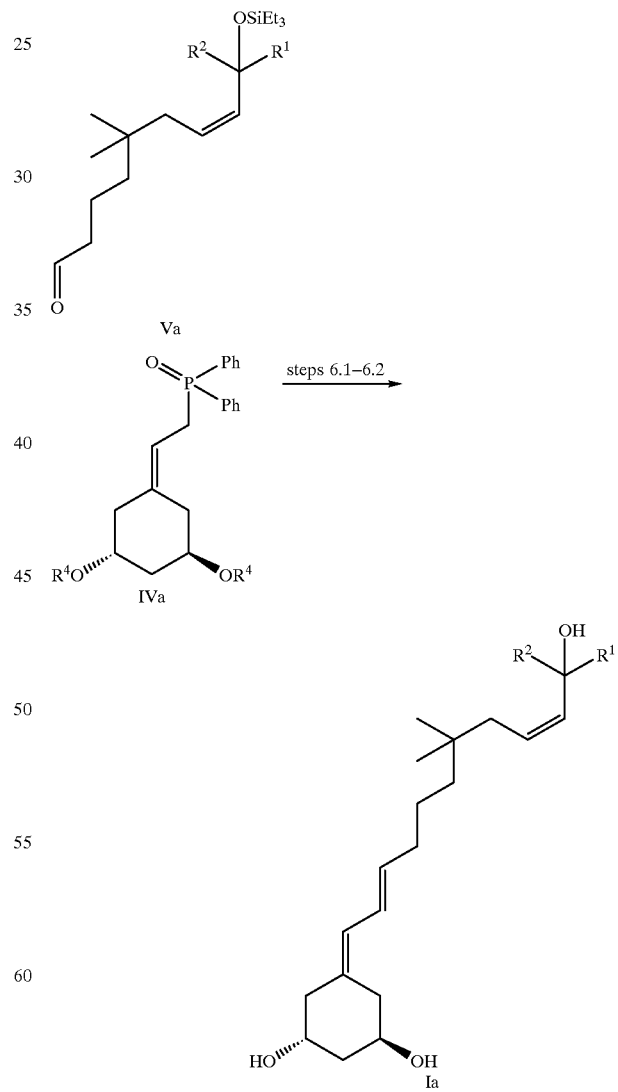

where the symbols are as defined above.

In step 6.1, phosphine oxides of formula IVa are reacted with aldehydes of formula Va, according to a Wittig-Horner reaction, to obtain fully hydroxy group protected retiferol derivatives of compounds of formula Ia.

The reaction is carried out in the presence of a strong base, such as LiN(SiMe$_3$)$_2$ or LDA, a preferably base is n-BuLi; and solvents are used such as hydrocarbons e.g. toluene or ethers preferably tetrahydrofurane (THF); at a reaction temperature from −100° to +60°, the preferred temperature for this reaction is in the range from −80° to 20°.

In step 6.2, the hydroxy protecting groups are cleaved, which can be effected by tetrabutylammonium fluoride (TBAF) in an inert solvent such as tetrahydrofuran to obtain compounds of formula Ia, as described in WO 99/43646.

Especially preferred are processes for the preparation of compounds of formula I wherein A represents a cis configurated double bond —CH═CH—.

Further preferred are processes for the preparation of compounds of formula I wherein A is —C═C—, for example (1R,3R)-5-[(2E,9Z)-12,12,12-trifluoro-11-hydroxy-7,7-dimethyl-11-trifluoromethyl-dodeca-2,9-dienylidene)-cyclohexane-1,3-diol.

In the following, the inventive processes for the preparation of intermediates IV is described. The synthesis of compound of formula Va is already described, as part of the reaction in schemes 4 and 5 (steps 4.1–4.4 and 5.1–5.3).

The compounds of formula IV may be prepared according to EP 0516410. However, it has been found that these compounds are prepared more effectively in a lower number of reaction steps and in a higher yield by the processes depicted in scheme 7 and 8, namely by a new process for the stereospecific synthesis of compounds of formula IVa.

A further aspect of the invention is thus the stereospecific synthesis of phosphinoxides of formula IVa, according to scheme 7.

wherein R$^3$ signifies lower alkyl or mono chlorinated lower alkyl and R$^4$ is a mono alkyl dimethyl-silyl group [Si(C$_{1-4}$-alkyl)Me$_2$].

In step 7.1, bis acylated ketones of formula IIa, which are prepared as described in steps 2.1–2.3, are reacted with commercial available Me$_3$SiCH$_2$COOEt in the presence of a base according to EP 0516410 B1, to obtain the corresponding protected unsaturated ester derivative of the compound of formula (12).

In step 7.2, the protected hydroxy groups of the unsaturated ester derivative of the compound of formula (12) are deprotected in the presence of a base, to obtain a compound of formula (12). The reaction is carried out as described in step 1.2.

Further, the above reaction is preferably carried out in methanol.

In step 7.3, the hydroxy groups of compound of formula (12) are protected by reaction with a protecting reagent in the presence of a base, to obtain protected derivative of compound of formula (13).

The above reaction is carried out with tert-butyldimethylsilyl triflate (TBSOTf) as protecting reagent or preferably with tert-butyldimethylsilyl chloride (TBSCl). Both protecting reagents yield to a hydroxy protected compound of formula (13), wherein R$^4$ is a tert-butyldimethyl-silyl group (TBS).

Further the reaction is carried out under the following conditions: in the presence of commercially available bases such as pyridine, dimethylpyridine (lutidine), NEt$_3$ or (isopropyl)$_2$NEt or preferably with imidazole; in solvents such as CH$_3$CN, CH$_2$Cl$_2$, THF or preferably N,N-dimethylformamide (DMF); at a reaction temperature from −60 to +50° or at a preferred temperature of 20°.

In step 7.4, the ester group of the compound of formula (13) is reduced in the presence of a reducing reagent such as Red-Al®, to a hydroxy compound of formula (14), as described in step 5.5a or in EP 0516410.

Scheme 7:

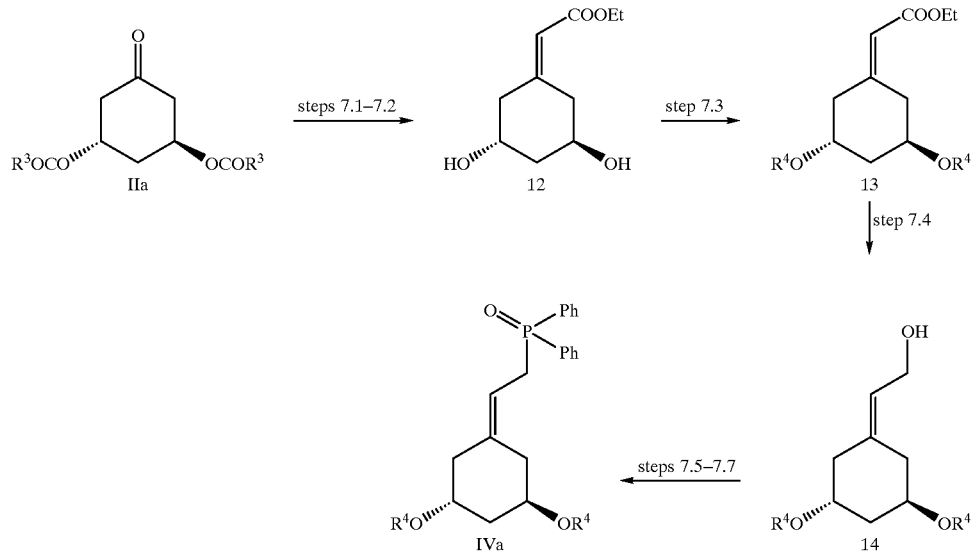

The reaction is carried out at a reaction temperature of −15°.

In step 7.5, the compound of formula (14) is treated with benzosulfochloride or preferably with tosyl chloride, in the presence of a base, to obtain the corresponding benzosulfo or tosylate derivative of the compound of formula (14).

The reaction is carried out under the following reaction conditions: with bases such as LDA, preferably n-BuLi; in solvents such as ethers, preferably THF, at a reaction temperature from −100° to 0°, preferably at a reaction temperature of −78°.

In steps 7.6 and 7.7, the tosylated or benzosulfonated derivative of the compound of formula (14) is reacted first with HPPh$_2$, in the presence of n-BuLi, and subsequently with H$_2$O$_2$ to obtain the corresponding phophine oxide of formula IVa. The reactions of step 7.6 and 7.7 are carried out according to EP 0516410.

A further embodiment of the invention is a second stereospecific process for the preparation of compounds of formula IVa, which is performed according to scheme 8, starting with compound of formula IIb, prepared according to scheme 3, Scheme 8:

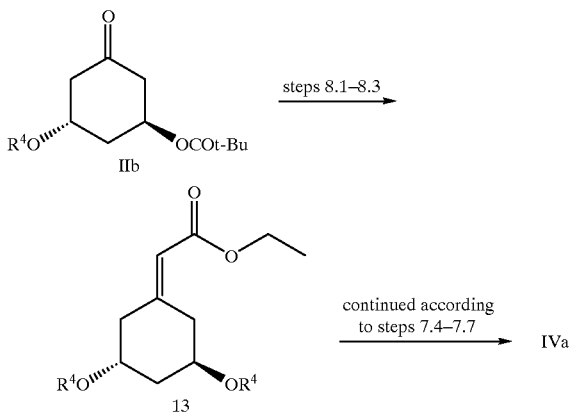

wherein the symbols are as defined above and R$^4$ is a mono alkyl dimethyl-silyl group [Si(C$_{1-4}$-alkyl)Me$_2$], preferably a mono (C$_1$–C$_4$)alkyl dimethyl-silyl group [Si(C$_{1-4}$-alkyl)Me$_2$], especially preferred is a tert-butyldimethyl-silyl group (TBS).

In step 8.1, compounds of formula IIb are reacted with commercial available Me$_3$SiCH$_2$COOEt in the presence of a base according to EP 0516410 or as described in step 7.1, to obtain the corresponding unsaturated ester derivative of compound of formula IIb.

In steps 8.2 and 8.3, the tert-butylOCO group of bis-hydroxy protected unsaturated ester derivative of compound of formula IIb is first cleaved to form a hydroxy group, obtaining the corresponding mono hydroxy derivative of compound of formula IIb, which is reacted with a protecting reagent as above defined, to obtain the protected ester compound of formula (13).

The reaction of step 8.2 is carried out, as described in step 3.4 and the reaction of step 8.3 is carried out, as described in step 7.3.

In summary (scheme B), the invention is thus concerned with new processes for the preparation of retiferol derivatives of formula I, namely by method A (steps 1.1–1.2) which comprises the coupling of ketones of formula II with compounds of formula III or by method B (steps 6.1–6.2) which comprises the coupling of phosphinoxides of formula IV with aldehydes of formula V.

The compounds of formula II are prepared according step 2.1–2.3 via an enzymatic hydrolyzation reaction or step 3.1–3.5 via an enzymatic acylation reaction.

The compounds of formula III are prepared according step 5.1–5.6 via compounds of formula V.

Scheme B:

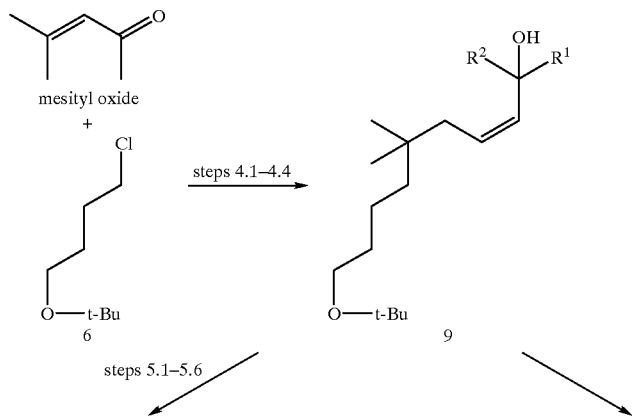

-continued

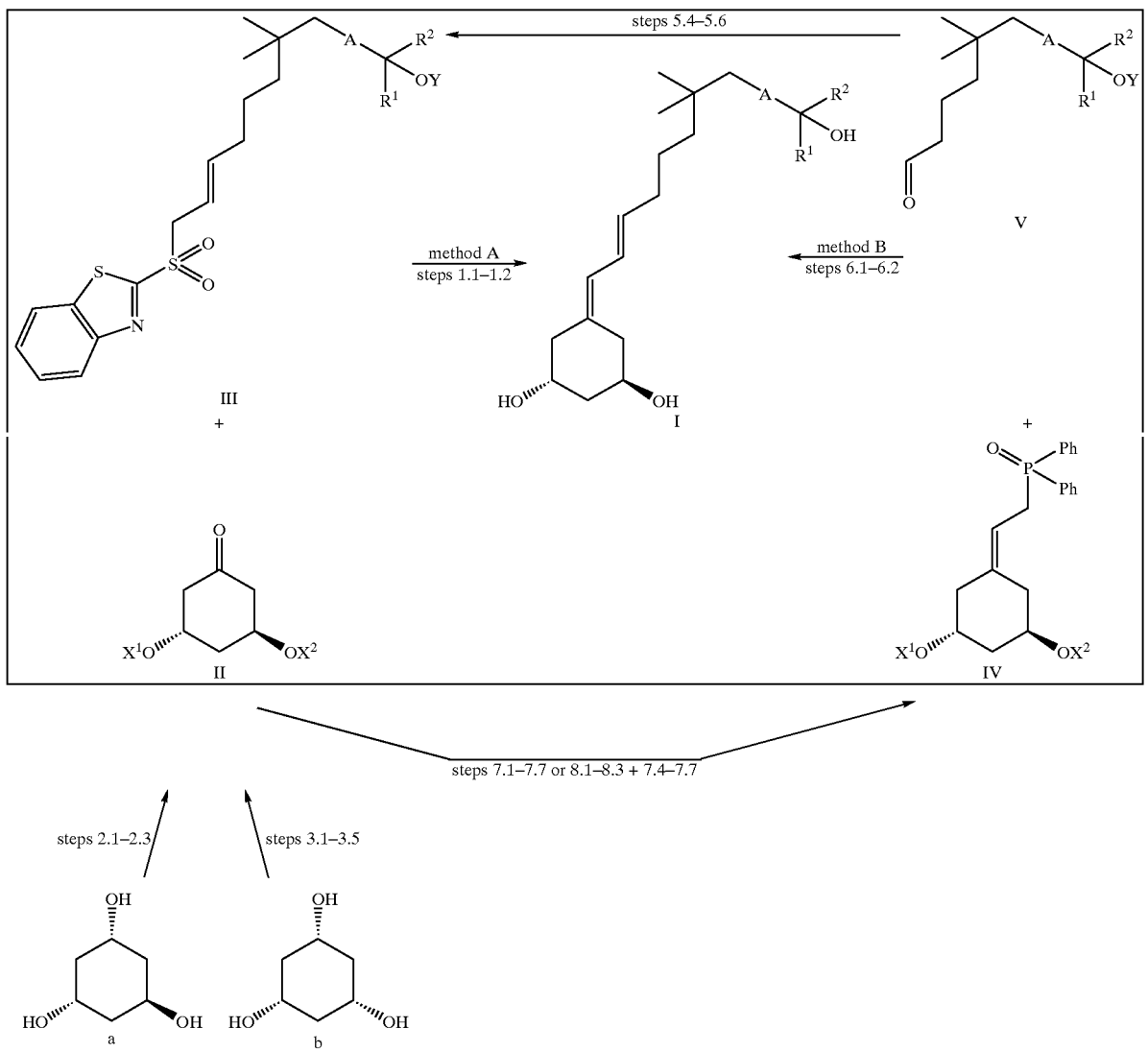

In these examples, the abbreviations used have the following significances.

| | |
|---|---|
| g.l.c. | gas liquid chromatography |
| t.l.c. | thin layer chromatography |
| IR | infrared spectroscopy |
| MS | mass spectroscopy |
| HPLC | high performance liquid chromatography |
| NMR | nuclear magnetic resonance spectroscopy |
| LDA | lithium diisopropylamide |
| DMF | dimethylformamide |
| AcOEt | ethyl acetate |
| MCPBA | 3-chloroperbenzoic acid |
| Oxone ® | (2KHSO$_5$*KHSO$_4$*K$_2$SO$_4$) |
| Red-Al ® | solution of sodium bis(2-methoxyethoxy) aluminium hydride |
| TBAF | tetrabutylammonium fluoride |
| TBSOTf | tert-butyldimethylsilyl triflate |
| TBSCl | tert-butyldimethylsilyl chloride |
| lutidine | dimethylpyridine |
| rt | room temperature |
| HV | high vacuum |
| min | minute(s) |
| h | hour(s) |

All temperatures are given in degrees Celsius (°).

EXAMPLE 1

1.1 Preparation of Acetic Acid (1R,3R)-3-Acetoxy-5-[(2E, 9Z)-12,12,12-trifluoro-7,7-dimethyl-11-triethylsilanyloxy-11-trifluoromethyl-dodeca-2,9-dienylidene]-cyclohexyl Ester To a solution of 322 mg of (2E,9Z)-2-(12,12,12-Trifluoro-7,7-dimethyl-11-triethylsilanyloxy-11-trifluoromethyl-dodeca-2,9-diene-1-sulfonyl)-benzothiazole in 2 ml of THF was added at −78° 0.5 ml of LiN(SiMe$_3$)2 (1.0 M in THF) and stirring of the red solution was continued for 30 min. To this solution was added at −78° a solution of 107 mg of (1R,3R)-1,3-diacetoxy-5-hydroxy-cyclohexane in 1 ml of THF over 10 min and stirring was continued for 5 h after which time t.l.c. indicated almost completion of the reaction.

The mixture was warmed to 22°, washed with sat. aqueous NH$_4$Cl-solution, the organic layer was dried over MgSO$_4$ and evaporated. The residue was chromatographed on a Lobar CN-column (Merck) with CH$_2$Cl$_2$/CH$_3$CN/hexane 15:5:200 to give 230 mg of the pure (t.l.c.) title compound as a colorless oil. IR (neat): 1735 m (CO); MS (EI): 613/1 (M–C$_2$H$_5$).

1.2 Preparation of (1R,3R)-5-[(2E,9Z)12,12,12-Trifluoro-11-hydroxy-7,7-dimethyl-11-trifluoromethyl-dodeca-2,9-dienylidene]-cyclohexane-1,3-diol To a solution of 50 mg of acetic acid (1R,3R)-3-acetoxy-5-[(2E,9Z)-12,12,12-trifluoro-7,7-dimethyl-11-triethylsilanyloxy-11-trifluoromethyl-dodeca-2,9-dienylidene]-cyclohexyl ester in 1.5 ml of CH$_3$H was added at 22° a solution of 37 mg of K$_2$CO$_3$ in 0.25 ml of water and stirring was continued for 8 h after which time t.l.c. indicated completion of the reaction. The mixture was evaporated and the residue was partitioned between dichloromethane and aqueous sat. NaCl, the organic layer was dried over MgSO$_4$ and evaporated. The residue was chromatographed on silica with hexane/AcOEt 2:1 to give 34 mg of the pure (t.l.c.) title compound as a colorless resin. IR (neat): 3345s (OH), 1661w and 1622w (C=C); MS (EI): 444/10 (M), 426/8 (M–H$_2$O).

EXAMPLE 2

2.1. Preparation of a 4:1-mixture of Trans- and All-cis-1,3,5-triacetoxy-cyclohexane To a suspension of 44.0 g of a 4:1-mixture of trans- and all-cis-1,3,5-cyclohexanetriol, prepared by crystallization of the commercially available 1:1-mixture of trans- and all-cis-1,3,5-cyclohexanetriol from ethanol/water (20:1) at −20°, and 110 ml of dry pyridine was added 157 ml of acetic anhydride at 22° and the solution was stirred at 45° for 4 h after which time GLC indicated completion of the reaction. The solution was evaporated to dryness and the residue was dissolved in dichloromethane. Washing of the organic layer with diluted hydrochloric acid, drying with MgSO$_4$ and evaporation of the solvent afforded 85.73 g of the pure (t.l.c.) title compound as a yellow oil. IR (neat): 1736s (C=O); MS (EI): 199/8 (M–OAc).

2.2. Preparation of (1R,3R)-1,3-Diacetoxy-5-hydroxy-cyclohexane

To a vigorously stirred mixture of 81.74 g of a 4:1-mixture of trans- and all-cis-1,3,5-triacetoxy-cyclohexane and 200 ml of cyclohexane was added subsequently 1300 ml of an aqueous 0.1 M NaCl solution and 50 ml of an aqueous 0.1 M sodium phosphate buffer (pH 7) and the pH was adjusted to 7.0 with aqueous 1.0 N NaOH. The stirred mixture was treated at 6° with a solution of 1.60 g of Lipase OF (Meito Sangyo) in 15 ml of aqueous 0.1 M NaCl-solution and the pH was kept at 7.0 by addition of 260 ml of an aqueous 1.0 N NaOH over 21.5 h. The mixture was extracted with dichloromethane, the organic layer was dried over Na$_2$SO$_4$ and evaporated. Chromatography (SiO$_2$, hexane/AcOEt, 3:2) gave 45.0 g of the pure (t.l.c.) title compound as a colorless oil, ee=99.5%. IR (neat): 3453m (OH), 1736s (C=O); MS (EI): 156/3 (M–AcOH).

2.3 Preparation of (1S,3S)-Acetic Acid 3-Acetoxy-5-oxo-cyclohexyl Ester

To a solution of 30.00 g of (1R,3R)-1,3-diacetoxy-5-hydroxy-cyclohexane in 400 ml of dichloromethane was subsequently added at 0° a solution of 1.155 g of KBr in 200 ml of water and 325 mg of 2,2,6,6-tetramethyl-piperidine-1-oxyl, radical and the pH was adjusted to 7.0 by addition of 1 ml of aqueous sat. NaHCO$_3$. The stirred mixture was treated simultaneously within 40 min with 107 g of NaOCl (10.6%) and 520 ml of aqueous 0.1 N hydrochloric acid keeping the pH at 7–8. The layers were separated, the organic layer was washed with 15% aqueous NaCl, dried over MgSO$_4$ and evaporated to give 28.93 g of the pure (t.l.c.) title compound as a yellow oil. IR (nujol): 1728s, br. (C=O).

EXAMPLE 3

3.1. Preparation of All-cis-5-(Tert-butyl-dimethyl-silanyloxy)-cyclohexane-1,3-diol To a suspension of 74.01 g of dry cis-cyclohexane-1,3,5-triol in 1480 ml of THF was added subsequently at 22° 95.72 g of tert-butyldimethylsilyl chloride and 62.33 g of triethylamine and the suspension was treated in one portion with 24.44 g of NaH (60% in oil) whereby the temperature rose slowly to 45° within 30 min. After 2 h at 40° the suspension was cooled to 10° and filtered. The filtrate was evaporated and the residue triturated at 22° with 750 ml of hexane. Filtration of the suspension and drying of the residue afforded 128.08 g of the pure (g.l.c.) title compound as a white solid, m.p. 117°–120°. IR (nujol): 3417m, 3338m and 3255m (OH); MS (EI): 245/3 (M–H).

3.2. Preparation of (1R,3S,5S)-3-(Tert-butyl-dimethyl-silanoxy)-5-hydroxy-cyclohex-1-yl Acetate To a stirred solution of 8.95 g of all-cis-5-(tert-butyl-dimethyl-silanyloxy)-cyclohexane-1,3-diol in 90 ml of vinyl acetate and 810 ml of ethyl acetate was added at 22° 0.895 g of Lipase QL (Meito Sangyo) and stirring was continued at 22° for 46 h after which time g.l.c. indicated completion of the reaction. The mixture was filtered, the filtrate evaporated and dried at 0.01 mbar to give 10.55 g of the pure (98.5%, g.l.c., ee=99.8%) title compound as a pale yellow oil. [α]$_D$+4.98° (CHCl$_3$, 1%); MS (EI): 231/2 (M–tert-butyl).

3.3. Preparation of (1R,3R,5S)-2,2-Dimethyl-propionic Acid 3-Acetoxy-5-(tert-butyl-dimethyl-silanyloxy)-cyclohexyl Ester To a solution of 10.67 g of (1R,3S,5S)-3-(tert-butyl-dimethyl-silanoxy)-5-hydroxycyclohex-1-yl acetate in 107 ml of THF was added at 22° 14.55 g of triphenylphosphine, the solution was cooled to 0° and treated dropwise with a solution of 11.81 g of diisopropyl azodicarboxylate and 5.67 g of pivalic acid in 85 ml of THF over 1 h and the solution was stirred at 0° for 1 h after which time t.l.c. showed completion of the reaction. The solution was evaporated, the residue triturated with 130 ml of hexane/AcOEt 9:1, the suspension was filtered and the filtrate evaporated. The residue was chromatographed on silica with hexane/AcOEt 30:1 to give 12.63 g of the pure (t.l.c.) title compound as a colorless oil. IR (neat): 1733s (C=O); MS (EI): 371/1 (M–H).

3.4. Preparation of (1R,3S,5R)-2,2-Dimethyl-propionic Acid 3-(Tert-butyl-dimethyl-silanyloxy)-5-hydroxy-cyclohexyl Ester A solution of 7.45 g of (1R,3R,5S)-2,2-dimethyl-propionic acid 3-acetoxy-5-(tert-butyl-dimethyl-silanyloxy)-cyclohexyl ester and 2.76 g of potassium carbonate in 52 ml of methanol and 24 ml of water was stirred at 22° for 6 h after which time t.l.c. showed completion of the reaction. The mixture was evaporated and the residue partitioned between dichloromethane and water. The organic layer was dried over MgSO$_4$ and evaporated to give 6.49 g of the pure (t.l.c.) title compound as a white solid, m.p. 39–42°. IR (nujol): 3240m (OH), 1731s (C=O); MS (EI): 273/10 (M–tert-butyl).

3.5. Preparation of (1S,3S)-2,2-Dimethyl-propionic Acid 3-(Tert-butyl-dimethyl-silanyloxy)-5-oxo-cyclohexyl Ester To a solution of 27.50 g of (1R,3S,5R)-2,2-dimethyl-propionic acid 3-(tert-butyl-dimethyl-silanyloxy)-5- hydroxy-cyclohexyl ester in 250 ml of dichloromethane was subsequently added at 0° a solution of 0.713 g of KBr and 2.656 g of NaHCO$_3$ in 250 ml of water and 200 mg of 2,2,6,6-tetramethyl-piperidine-1-oxyl, radical. The stirred mixture was treated at 0° with 61.9 g of NaOCl (11.0%) over 1 h after which time t.l.c. showed completion of the reaction. The layers were separated, the organic layer was washed with 15% aqueous NaCl, dried over MgSO$_4$ and evaporated to give 27.24 g of the pure (t.l.c.) title compound as a yellow oil. IR (neat): 1728s (C=O). MS (EI): 271/5 (M−tert-butyl).

EXAMPLE 4

4.1. Preparation of 8-Tert-butoxy-4,4,-dimethyl-octan-2-one

To a solution of 49.00 g of 4-chlorobutanol in 120 ml of hexane and 360 ml of tert-butylmethyl ether was added 11.3 g Amberlyst (H-15) and the mixture was treated at 32°–38° with isobutene until take-up of the gas ceased (4.5 h). The mixture was filtered and the filtrate evaporated to dryness. The crude 4-chlorobutyl tertbutyl ether (70.0 g) was dissolved in 400 ml of THF and the resulting solution was added dropwise to a suspension of 10.33 g of magnesium powder in 20 ml of THF at reflux temperature over 40 min and the reaction was initiated with a small amount of iodine. The suspension was heated at reflux temperature for 3.5 h, cooled to 22° and added dropwise to a suspension of 8.58 g of copper (I) iodide in 90 ml of THF at −10° over 30 min. and stirring was continued at −10° for 15 min. The dark solution was treated at −15° to −20° with 41.72 g of mesityl oxide over 15 min and stirring was continued at −20° for 1 h. The suspension was washed with 600 ml of 15% aqueous NH$_4$Cl and sat. aqueous NaCl, the organic layer was dried over MgSO$_4$ and evaporated to give 83.71 g of the crude title compound as a pale brown oil. IR (neat): 1718s (C=O); MS (EI): 213/2 (M−CH$_3$).

4.2–4.3. Preparation of 10-Tert-butoxy-1,1,1-trifluoro-6,6-dimethyl-2-trifluoromethyl-dec-3-yn-2-ol To a solution of 27.62 g of diisopropyl amine in 28 ml of THF was added at −78° 171 ml of n-BuLi (1.6 M in hexane) the solution was warmed to 0° for 30 min and cooled to −78°. The LDA-solution was treated at −78° with a solution of 59.38 g of the crude 10-tert-butoxy-1,1,1-trofluoro-6,6-dimethyl-2-trifluoromethyl-dec-3-yn-2-ol in 20 ml of THF over 40 min and stirring was continued at −78° for 1 h. The yellow solution was treated at −78° with 47.11 g of diethylchlorophosphate over 30 min, the mixture was warmed to 22° over 2 h and stirring was continued at 22° for 2 h. The suspension was added at −78° dropwise to a solution of LDA, prepared with 52.62 g diisopropyl amine, 325 ml of n-BuLi (1.6 M in hexane) and 60 ml of THF as described above, over 20 min and stirring was continued at −78° for 2 h. The suspension containing the anion of 8-tert-butoxy-4,4-dimethyl-oct-1-yne was treated at −78° with 60.0 g of hexafluoroacetone over 10 min and stirring was continued at −78° for 30 min. The suspension was washed with 300 ml of sat. aqueous NH$_4$Cl and sat. aqueous NaCl, the organic layer was dried over MgSO$_4$ and evaporated to give 107.9 g of crude product. The material was crystallized from 160 ml of hexane at −20° to give 43.00 g of the pure title compound as a white solid, m.p. 66–67°. The mother liquor was purified by chromatography on silica with hexane/AcOEt 19:1 to give 21.1 g of the pure title compound. IR(nujol): 3157m (OH), 2242m (C,C-triple bond); MS(EI): 361/20 (M−CH$_3$).

4.4. Preparation of (Z)-10,10,10-Trifluoro-5,5-dimethyl-9-trifluormethyl-dec-7-ene-1,9-diol A suspension of 22.13 g of 10-tert-butoxy-1,1,1-trifluoro-6,6-dimethyl-2-trifluoromethyl-dec-3-yn-2-ol, 220 ml of tert-butylmethyl ether and 3.32 g of Lindlar catalyst was hydrogenated at 22° and 1 bar for 1.5 h after which time hydrogen up-take ceased. The suspension was filtered, the filtrate evaporated and the residue, containing pure (Z)-10-tert-butoxy-1,1,1, -trifluoro-6,6-dimethyl-2-trifluoromethyl-dec-3-en-2-ol, was dissolved in 44 ml of isopropanol. The solution was treated with 22.8 g of 50% aqueous H$_2$SO$_4$ and the mixture was heated to 90° for 2 h after which time g.l.c. indicated completion of the reaction. The mixture was evaporated, the residue partitioned between dichloromethane and saturated NaHCO$_3$ solution and the aqueous layer was extracted several times with dichloromethane. The combined organic layers were dried over MgSO$_4$ and evaporated to give 17.97 g of the pure title compound as a colorless oil.

EXAMPLE 5

5.1.1 Preparation of (Z)-10,10,10-Trifluoro-9-hydroxy-5,5-dimethyl-9-trifluoromethyl-dec-7-enal To a solution of 3.39 g of (Z)-10,10,10-trifluoro-5,5-dimethyl-9-trifluormethyl-dec-7-ene-1,9-diol in 15 ml of dichloromethane was added a solution of 90 mg of KBr and 336 mg of NaHCO$_3$ in 14 ml of water and 8.5 mg of 2,2,6,6-tetramethylpiperidin-1-oxyl, radical, and the mixture was treated at 0° under vigorous stirring with 8.00 g of aqueous NaOCl (10.8%) over 1 h. The organic layer was washed with sat. aqueous NaCl, dried over MgSO$_4$ and evaporated to give 2.92 g of the pure (t.l.c.) title compound as a pale yellow oil. IR (neat): 1718s (C=O).

5.1.2 Preparation of (Z)-10,10,10-Trifluoro-5,5-dimethyl-9-triethylsilanyloxy-9-trifluoromethyl-dec-7-enal To a solution of 6.73 g of (Z)-10,10,10-trifluoro-9-hydroxy-5,5-dimethyl-9-trifluoromethyl-dec-7-enal in 67 ml of THF was added at 22° subsequently 2.55 g of triethylamine, 0.128 g of 4-dimethylamino pyridine and 3.92 g of triethylsilyl chloride and the solution was stirred at 22° for 1.5 h after which time g.l.c. indicated completion of the reaction. The suspension was evaporated, the residue dissolved in dichloromethane and washed with 0.1 N of aqueous hydrochloric acid and with sat. aqueous NaCl. The organic layer was dried over MgSO$_4$, evaporated and the residue was chromatographed over silica with hexane/AcOEt 15:1 to give 7.50 g of the pure (99%, g.l.c.) title compound as a colorless liquid. IR (neat): 1729s (C=O), 1661w (C=C). MS (El): 405/10 M−C$_2$H$_5$).

5.1.3 Preparation of (2E,9Z)-12,12,12-Trifluoro-7,7-dimethyl-11-triethylsilanyloxy-11-trifluoromethyl-dodeca-2,9-dienoic Acid Ethyl Ester Method 1: To a suspension of 292 mg of potassium tert-butylate in 8 ml of toluene was added at 0° a solution of 583 mg of triethyl phosphonoacetate in 2 ml of toluene and stirring was continued at 22 for 1 h. The suspension was cooled to −78° and treated dropwise with a solution of 870 mg of (Z)-10,10,10-trifluoro-5,5-dimethyl-9-triethylsilanyloxy-9-trifluoromethyl-dec-7-enal in 2 ml of toluene after which t.l.c. showed completion of the reaction. The suspension contained pure (2E,9Z)-12,12,12-Trifluoro-7,7-dimethyl-11-triethylsilanyloxy-11-trifluoromethyl-dodeca-2,9-dienoic acid ethyl ester (IR (neat): 1724s (C=O), 1655m (C=C); MS (EI): 475/25 (M−C$_2$H$_5$).

Method 2: To a solution of 1.42 g of diisopropyl amine in 87 ml of THF was added at −10° 8.8 ml of n-BuLi (1.6 M in THF), the solution was cooled to −78° and treated with 2.31 g of ethyl (trimethylsilyl) acetate and stirring was continued for 15 min. The yellow solution was treated with a solution of 3.14 g of (Z)-10,10,10-trifluoro-5,5-dimethyl-9-triethylsilanyloxy-9-trifluoromethyl-dec-7-enal in 17 ml of THF and stirring was continued at −78° for 2 h after which time t.l.c. indicated completion of the reaction. The mixture was washed with sat. aqueous NH$_4$Cl- and NaCl-solution, the organic layer was dried over MgSO$_4$ and evaporated. The residue was chromatographed on silica with hexane/AcOEt 50:1 to give 0.97 g of pure (t.l.c.) (2Z,9Z)-12,12,12-Trifluoro-7,7-dimethyl-11-triethylsilanyloxy-11-trifluoromethyl-dodeca-2,9-dienoic acid ethyl ester as a colorless oil. IR (neat): 1723s (C=O), 1645m (C=C); MS (EI): 505/0.5 (M+H), 475/35 (M−C$_2$H$_5$). The second fraction contained 2.01 g of pure (t.l.c.) title compound (2E,9Z)-12,12,12-trifluoro-7,7-dimethyl-11-triethylsilanyloxy-11-trifluoromethyl-dodeca-2,9-dienoic acid ethyl ester as a colorless oil. IR (neat): 1724s (C=O), 1655m (C=C); MS (EI): 475/25 (M−C$_2$H$_5$).

5.1.4 Preparation of (2E,9Z)-12,12,12-Trifluoro-7,7-dimethyl-11-triethylsilanyloxy-11-trifluoromethyl-dodeca-2,9-dien-1-ol To a solution of 10.09 g of (2E,9Z)-12,12,12-Trifluoro-7,7-dimethyl-11-triethylsilanyloxy-11-trifluoromethyl-dodeca-2,9-dienoic acid ethyl ester in 100 ml of toluene was added at −78° 40.0 ml of diisobutylaluminiumhydride (1.2 M in toluene) and stirring was continued for 30 min after which time t.l.c. indicated completion of the reaction. The mixture was washed with sat. aqueous NH$_4$Cl-solution and water, the organic layer was dried over MgSO$_4$ and evaporated to give 8.92 g of the pure (t.l.c.) title compound as a pale yellow oil. IR (neat): 3332m, br. (OH), 1669w (C=C).

5.1.5 Preparation of (2E,9Z)-2-(12,12,12-Trifluoro-7,7-dimethyl-11-triethylsilanyloxy-11-trifluoromethyl-dodeca-2,9-dienylsulfanyl)-benzothiazole To a solution of 6.59 g of 2-mercapto-benzothiazole and 7.87 g of triphenylphosphine in 65 ml of THF was added at 0° a solution of 9.25 g of (2E,9Z)-12,12,12-Trifluoro-7,7-dimethyl-11-triethylsilanyloxy-11-trifluoromethyl-dodeca-2,9-dien-1-ol in 35 ml of THF which was followed by addition of 8.09 g of diisopropyl azodicarboxylate over 20 min and stirring was continued at 0° for 1 h after which time t.l.c. indicated completion of the reaction. The mixture was washed with sat. aqueous NH$_4$Cl- and NaCl-solution, the organic layer was dried over MgSO$_4$ and evaporated. The residue was chromatographed on silica with hexane/AcOEt 9:1 to give 11.13 g of the pure (t.l.c.) title compound as a yellow oil. IR (neat): 1663w (C=C). MS (EI): 611/7 (M).

5.1.6 Preparation of (2E,9Z)-2-(12,12,12-Trifluoro-7,7-dimethyl-11-triethylsilanyloxy-11-trifluoromethyl-dodeca-2,9-diene-1-sulfonyl)-benzothiazole To a solution of 10.50 g of (2E,9Z)-2-(12,12,12-Trifluoro-7,7-dimethyl-11-triethylsilanyloxy-11-trifluoromethyl-dodeca-2,9-dienylsulfanyl)-benzothiazole in 95 ml of ethanol was added at 0° a solution of 2.12 g of ammonium heptamolybdate-tetrahydrate in 7.1 ml of hydrogen peroxide (35%) over 10 min and stirring was continued at 0° for 3 h and at 22° for 5 h after which time t.l.c. indicated completion of the recation. The yellow suspension was cooled to 0°, treated with 60 ml of an aqueous solution of Na$_2$SO$_3$ (10%) and the mixture was evaporated. The residue was partitioned between dichloromethane and water, the organic layer was dried over MgSO$_4$ and evaporated. The residue was chromatographed on silica with hexane/AcOEt 1:1 to give 11.13 g of the pure (t.l.c.) title compound as a colorless oil. IR (neat): 1149s (SO$_2$); MS (EI): 614/7 (M−C$_2$H$_5$).

EXAMPLE 6

6.1 Preparation of (1R,3R)-5-[(2E,9Z)12,12,12-trifluoro-11-hydroxy-7,7-dimethyl-11-trifluoromethyl-dodeca-2,9-dienylidene]-cyclohexane-1,3-diol To a solution of 47.96 g of [(3R,5R)-bis-(tert-butyl-dimethyl-silanyloxy)-cyclohexylidene]-ethyl-diphenylphosphine oxide in 480 ml of THF was added at −78° 55.5 ml of n-BuLi (1.6 M in hexane) over 1 h and stirring of the red solution was continued for 30 min. To this solution was added at −78° a solution of 26.07 g of (Z)-10,10,10-trifluoro-5,5-dimethyl-9-triethylsilanyloxy-9-trifluoromethyl-dec-7-enal in 130 ml of THF over 1 h, the yellow solution was warmed to 22° over 3 h and stirring was continued at 22° for 63 h. The pale yellow suspension was washed with a sat. aqueous NH$_4$Cl- and NaCl-solution, dried over MgSO$_4$ and evaporated. The residue was chromatographed on silica with hexane/AcOEt 19:1 and the fractions containing the coupling product (R$_f$=0.64, hexane/AcOEt 9:1) and the triethylsilyl-deprotected coupling product (R$_f$=0.44, hexane/AcOEt 9:1) were combined and evaporated. The residue was dissolved in 200 ml of TBAF (1.0 M in THF), the yellow solution was heated to 45° for 8 h and stirring was continued at 22° for 19 h. The red solution was evaporated, the residue partitioned between AcOEt and water, the organic layer was dried over MgSO$_4$ and evaporated. The residue was chromatographed over silica with hexane/isopropylOH 4:1 to give 18.17 g of a 9:1-mixture of the 2E- and 2Z-isomers which were separated by preparative HPLC chromatography (Kromasil, 10–100, heptane/isopropylOH 92:8) to give 15.44 g of the pure (HPLC) title compound as a colorless resin. IR (neat): 3345s (OH), 1661w and 1622w (C=C); MS (EI): 444/10 (M), 426/8 (M−H$_2$O).

EXAMPLE 7

7.1 Preparation of ((3R,5R)-Diacetoxy-cyclohexylidene)-acetic Acid Ethyl Ester

To a solution of 1000 ml of a 0.2 M LDA-solution was added at −78° a solution of 33.05 g of ethyl (trimethylsilyl)acetate in 100 ml of THF within 1 h followed by addition of a solution of 21.42 g of (1S,3S)-acetic acid 3-acetoxy-5-oxo-cyclohexyl ester in 150 ml of THF and stirring was continued at −78° for 1.5 h after which time t.l.c. showed completion of the reaction. The yellow solution was washed with aqueous sat. NH$_4$Cl and aqueous sat. NaCl, the organic layer was dried over MgSO$_4$, evaporated and the residue was chromatographed on silica with hexane/AcOEt (4:1) to give 23.57 g of the pure (t.l.c.) title compound as a pale yellow oil. IR (neat): 1738s and 1710s (C=O), 1656s (C=C).

7.2 Preparation of a 3:1-mixture of ((3R,5R)-Dihydroxy-cyclohexylidene)-acetic Acid Ethyl and Methyl Ester To a solution of 21.60 g of ((3R,5R)-diacetoxy-cyclohexylidene)-acetic acid ethyl ester in 160 ml of methanol was added at 0° a solution of 21.0 g K$_2$CO$_3$ in 74 ml of water and the solution was stirred vigorously at 22° for 6 h after which time t.l.c. showed completion of the reaction. The mixture was evaporated, the residue partitioned between aqueous sat. NaCl and dichloromethane and the aqueous layer was extracted several times with dichloromethane. The combined organic layers were dried over MgSO$_4$ and evaporated to give 14.75 g of the pure (t.l.c.) title compounds as a yellow oil. IR(neat): 3392s (OH), 1712s (C=O), 1651s (C=C); MS(EI): 201/2 (M+H+), 182/15 (M−H$_2$O).

7.3 Preparation of a 3:1-mixture of [(3R,5R)-Bis-(tert-butyl-dimethyl-silanyloxy)-cyclohexylidene]-acetic Acid Ethyl and Methyl Ester To a solution of 13.80 g of a 3:1-mixture of ((3R,5R)-dihydroxy-cyclohexylidene)-acetic acid ethyl and methyl ester in 70 ml of DMF was added at 22° 23.56 g of tert-butyldimethylsilyl chloride and 10.32 g of imidazole keeping the temperature at 22°. The suspension was stirred at 22° for 3 h after which time t.l.c. showed completion of the reaction. The mixture was diluted at 10° with 70 ml of toluene and 70 ml of water, the organic layer was washed several times with water and evaporated to give 29.05 g of the pure (t.l.c.) title compound as a pale yellow oil. IR (neat): 1721s (C=O), 1655m (C=C).

7.4 Preparation of [(3R,5R)-Bis-(tert-butyl-dimethyl-silanyloxy)-cyclohexylidene]-ethanol To a solution of 27.00 g of a 3:1-mixture of [(3R,5R)-bis-(tert-butyl-dimethyl-silanyloxy)-cyclohexylidene]-acetic acid ethyl and methyl ester in 270 ml of toluene was added at −15° 43 ml of Red-Al® (3.5 M) over 30 min and stirring was continued at −15° for 1 h after which time t.l.c. showed completion of the reaction. The yellow solution was slowly diluted at −15° to 0° with 140 ml of water and the emulsion was diluted with 135 ml of aqueous 1 N NaOH. The organic layer was washed several times with water, dried over MgSO$_4$ and evaporated to give the pure (t.l.c.) title compound as a colorless wax. [α]$_D$+16.4° (CHCl$_3$, 1%); IR (nujol): 3240s, br. (OH), 1675w (C=C); MS (EI): 371/3 (M−CH$_3$).

7.5 Preparation of [(3R,5R)-Bis-(tert-butyl-dimethyl-silanyloxy)-cyclohexylidene]-ethyl-diphenylphosphine Oxide To a solution of 9.67 g of [(3R,5R)-bis-(tert-butyl-dimethyl-silanyloxy)-cyclohexylidene]-ethanol in 97 ml of THF was subsequently added at 0° 16.4 ml of n-BuLi (1.6 M in hexane) over 20 min and a solution of 4.96 g of toluene-4-sulfonyl chloride in 50 ml over 30 min and stirring was continued at 0° for 2.5 h. The pale yellow solution was treated over 1 h at 0° with a solution of lithium diphenylphosphide, prepared by addition of 17.2 ml of n-BuLi (1.6 M in hexane) to a solution of 5.38 g of diphenylphosphine in 43 ml of THF at 0° over 1 h, and stirring was continued at −25° for 16 h. The yellow mixture was slowly treated with 5 ml of water and evaporated. The residue was diluted with 230 ml of dichloromethane and 210 ml of water and the vigorously stirred mixture was treated at 22° with 24.3 g of hydrogen peroxide (35%) and stirring was continued for 3.5 h. The organic layer was washed with aqueous sat. NaHCO$_3$ and water, dried over MgSO$_4$, evaporated and the residue was chromatographed on silica with hexane/AcOEt 2:1 to give 8.9–10.7 g of the pure (t.l.c.) title compound as a white solid, m.p. 66–73°. IR (KBr): 1180s (P=O); MS (EI): 555/3 (M−CH$_3$).

Upon reading the present specification, various alternative embodiments become obvious to the skilled artisan. These variations are to be considered within the scope of the spirit of the subject invention, which is only to be limited by the claims that follow and their equivalence.

What is claimed is:

1. A process for preparing a compound of the formula:

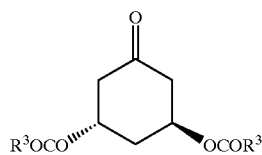

IIa wherein R$^3$ is lower alkyl or mono-chlorinated lower alkyl;

which comprises:

a) protecting the hydroxy groups of the trans/cis/trans compound of the formula:

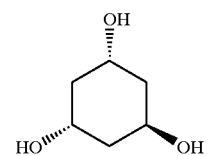

a or protecting the hydroxy groups of the all cis 1,3,5-trihydroxycyclohexane, to obtain the compound of the formula:

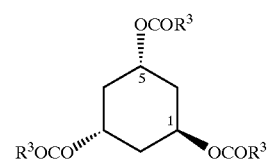

1 wherein R$^3$ is lower alkyl or mono-chlorinated lower alkyl), or in the case of the all cis 1,3,5-trihydroxycyclohexane, obtaining the protected all cis 1,3,5-trihydroxycyclohexane wherein the hydrogen atoms of the hydroxy groups have been replaced by R$^3$ as above;

b) hydrolyzing the R$^3$CO-group in the 5-position in a biphasic water/organic solvent system in an enzymatic reaction to obtain a product of formula (2):

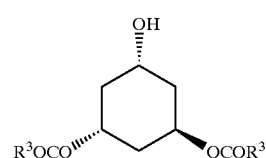

2 wherein R$^3$ is as above; and c) oxidizing the hydroxy group to obtain a compound of formula Ia.

2. The process according to claim 1, wherein the enzymatic reaction lipases of the EC-class 3.1.1.3 or 3.1.1.34 are used.

3. A process for preparing a compound of the formula:

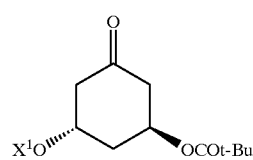

IIb wherein X$^1$ is Si(C$_{1-4}$-alkyl)Me$_2$ or R$^3$CO— wherein R$^3$ is lower alkyl or mono-chlorinated lower alkyl;

which comprises:

a) protecting one hydroxy group of a compound of the formula:

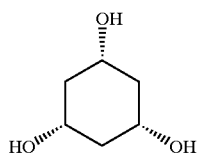

to obtain a compound of the formula:

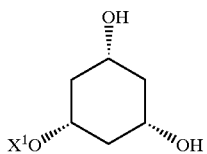

wherein $X^1$ is as above;
b) acylating via an enzyme a further hydroxy group of a compound of the formula (3) in a non-aqueous acylation solvent to obtain a compound of the formula:

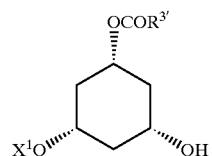

wherein $X^1$ is as above and $R^{3'}$ is methyl;
c) inverting the configuration of the carbon atom which carries the remaining unprotected hydroxy group in compound of formula (4);
d) cleaving the $R^{3'}OC$— group to form a hydroxy derivative; and
e) oxidizing the hydroxy group to obtain a compound of formula IIb.

4. The process according to claim 3, wherein enzyme is a lipase of the EC-class 3.1.1.3 or lipoprotein lipases of the EC-class 3.1.1.34.

* * * * *

UNITED STATES PATENT AND TRADEMARK OFFICE
CERTIFICATE OF CORRECTION

PATENT NO.    : 6,403,346 B1                                      Page 1 of 1
DATED         : June 11, 2002
INVENTOR(S)   : Hans Hilpert and Beat Wirz It is certified that error appears in the above-identified patent and that said Letters Patent is hereby corrected as shown below:

<u>Column 36,</u>
Line 46, delete "Ia" and insert -- IIa --

Signed and Sealed this

Twenty-sixth Day of November, 2002

Attest:

Attesting Officer

JAMES E. ROGAN
*Director of the United States Patent and Trademark Office*